United States Patent
Dalla-Betta et al.

(10) Patent No.: US 10,696,941 B2
(45) Date of Patent: Jun. 30, 2020

(54) METHOD AND APPARATUS FOR GROWING MICROBIAL CULTURES THAT REQUIRE GASEOUS ELECTRON DONORS, ELECTRON ACCEPTORS, CARBON SOURCES, OR OTHER NUTRIENTS

(71) Applicant: Kiverdi, Inc., Berkeley, CA (US)

(72) Inventors: Peter Dalla-Betta, Hayward, CA (US); John S. Reed, Berkeley, CA (US)

(73) Assignee: Kiverdi, Inc., Pleasanton, CA (US)

( * ) Notice: Subject to any disclaimer, the term of this patent is extended or adjusted under 35 U.S.C. 154(b) by 0 days.

(21) Appl. No.: 14/839,074

(22) Filed: Aug. 28, 2015

(65) Prior Publication Data
US 2016/0102287 A1 Apr. 14, 2016

Related U.S. Application Data

(63) Continuation of application No. 13/715,430, filed on Dec. 14, 2012, now Pat. No. 9,157,058.

(60) Provisional application No. 61/570,773, filed on Dec. 14, 2011.

(51) Int. Cl.
| | |
|---|---|
| *C12M 3/00* | (2006.01) |
| *C12M 1/00* | (2006.01) |
| *C12N 1/20* | (2006.01) |
| *C12M 1/12* | (2006.01) |
| *C12M 1/34* | (2006.01) |
| *C12M 1/36* | (2006.01) |

(52) U.S. Cl.
CPC ............. *C12N 1/20* (2013.01); *C12M 23/40* (2013.01); *C12M 25/00* (2013.01); *C12M 29/02* (2013.01); *C12M 29/18* (2013.01); *C12M 29/20* (2013.01); *C12M 29/24* (2013.01); *C12M 41/44* (2013.01); *C12M 41/46* (2013.01); *C12M 41/48* (2013.01); *C12M 43/04* (2013.01)

(58) Field of Classification Search
CPC ...... C12M 23/58; C12M 29/00; C12M 29/18; C12M 29/24; C12M 29/14
See application file for complete search history.

(56) References Cited

U.S. PATENT DOCUMENTS

| | | | | |
|---|---|---|---|---|
| 5,500,112 | A * | 3/1996 | McDonald | ......... B01D 21/0003 |
| | | | | 210/151 |
| 6,299,774 | B1 * | 10/2001 | Ainsworth | ................ C02F 3/28 |
| | | | | 210/178 |
| 6,342,378 | B1 * | 1/2002 | Zhang | .................... C12M 21/04 |
| | | | | 210/203 |
| 2011/0136213 | A1 * | 6/2011 | Stewart | .................. C12M 21/04 |
| | | | | 435/262 |

(Continued)

OTHER PUBLICATIONS

Madigan et al "Growth of the photosynthetic bacterium Rhodopseudomonas capsulata chemoautotrophically in darkness with H2 as the energy source" J Bacteriol.; 137(1): 524-30 ;1979.*

*Primary Examiner* — Nathan A Bowers
(74) *Attorney, Agent, or Firm* — FisherBroyles, LLP; Jill Jacobson

(57) ABSTRACT

Compositions and methods and apparatus for growth and maintenance of microorganisms and/or bioprocesses using one or more gases as electron donors, electron acceptors, carbon sources, or other nutrients, and for a bioprocess that converts hydrogen and carbon dioxide, or syngas, or producer gas into lipid products, bio-based oils, or other biochemical products.

16 Claims, 12 Drawing Sheets

(56) References Cited

U.S. PATENT DOCUMENTS

| | | | | |
|---|---|---|---|---|
| 2011/0318778 A1* | 12/2011 | Petersen | ............. | C05F 17/0018 |
| | | | | 435/41 |
| 2012/0156744 A1* | 6/2012 | MacDonald | ............ | C02F 3/286 |
| | | | | 435/155 |
| 2012/0183987 A1* | 7/2012 | Gevaert | ................. | C12M 23/34 |
| | | | | 435/29 |
| 2013/0149755 A1* | 6/2013 | Reed | ..................... | C12P 7/6463 |
| | | | | 435/135 |

* cited by examiner

Fig 7 — Pressure improves gas transfer into media

- Rate of transfer increases with increase in pressure
- Gas transfer rate = $K_L a\,(C^*_L - C_L)$ $K_L a$ = liquid mass-transfer coefficient times the available surface area
$C^*_L$ = gas concentration in the gas phase
$C_L$ = gas concentration in the aqueous phase Fig 8  CO2 to Organic Compounds Using Oxyhydrogen Reaction

METHOD AND APPARATUS FOR GROWING MICROBIAL CULTURES THAT REQUIRE GASEOUS ELECTRON DONORS, ELECTRON ACCEPTORS, CARBON SOURCES, OR OTHER NUTRIENTS

RELATED APPLICATIONS

This application is a continuation of U.S. patent application Ser. No. 13/715,430, filed Dec. 14, 2012, which claims the benefit under 35 U.S.C. § 119(e) to U.S. Provisional Application No. 61/570,773, filed Dec. 14, 2011 and entitled "METHOD AND APPARATUS FOR GROWING MICROBIAL CULTURES THAT REQUIRE GASEOUS ELECTRON DONORS, ELECTRON ACCEPTORS, CARBON SOURCES, OR OTHER NUTRIENTS," and which is incorporated herein by reference in its entirety for all purposes.

FIELD OF INVENTION

The present invention falls within the technical areas of biofuels, bioprocesses, bioreactors, bioremediation, carbon capture, carbon dioxide-to-fuels, carbon recycling, carbon sequestration, energy storage, gas dissolution, gas-to-liquids, mass transfer, syngas-to-liquids, waste energy to fuels, syngas conversions, and renewable/alternative and/or low carbon dioxide emission sources of energy. Specifically the present invention is a unique example of the use of a bioreactor to contain biocatalysts, and in particular biocatalysts that fix carbon dioxide and/or other forms of inorganic carbon and/or other C1 carbon sources into longer carbon chain organic chemical products in a non-photosynthetic process powered by low carbon emission energy sources and/or waste energy sources where the bioprocess utilizes a gaseous carbon source or electron donor or electron acceptor. In addition the present invention involves the production of chemical co-products that are co-generated through carbon-fixation reaction steps and/or non-biological reaction steps as part of an overall inorganic carbon conversion process or syngas conversion process. The present invention can enable the effective and economic capture of carbon dioxide from the atmosphere or from a point source of carbon dioxide emissions as well as the economic use of waste energy sources and/or renewable energy sources and/or low carbon emission energy sources and/or syngas sources, for the production of high energy density oleochemicals.

BACKGROUND

Great interest and resources have been directed towards developing technologies that use renewable energy or waste energy or low cost syngas or producer gas for the production of useful organic chemicals, which provide alternatives to chemicals, materials and fuels derived from petroleum or other fossil sources; as well as chemicals, materials and fuels derived from purpose grown crops that compete with food production or negatively impact natural habitats. These alternative approaches to the sustainable production of organic chemicals can involve the conversion of carbon dioxide, or other relatively low value carbon sources such as but not limited to lignocellulosic energy crops, crop residues, bagasse, saw dust, forestry residue, food waste, municipal solid waste, sewage, waste carpet, biogas, landfill gas, stranded natural gas, or pet coke. The conversion of low value fixed carbon sources such as but not limited to lignocellulosic energy crops, crop residues, bagasse, saw dust, forestry residue, food waste, municipal solid waste, sewage, waste carpet, biogas, landfill gas, stranded natural gas, or pet coke, to organic chemicals, often involves a syngas or producer gas intermediate—a stream of gas that is rich in hydrogen and/or carbon monoxide, which can be generated from the said fixed-carbon source using gasifier, partial oxidation, steam reforming, or pyrolysis technologies known in the art. Most of the focus in the area of $CO_2$ conversion has been placed on biological approaches that utilize photosynthesis to fix $CO_2$ into biomass or organic end products, while some effort has been directed at fully abiotic and chemical processes for fixing $CO_2$.

A type of $CO_2$-to-organic chemical approach that has received relatively less attention is hybrid chemical/biological processes where the biological step is limited to the fixation of C1 compounds, such as $CO_2$, alone, which corresponds to the dark reaction of photosynthesis, while reducing equivalents needed for carbon-fixation are generated through an abiotic process, thus substituting for the light reaction of photosynthesis. The potential advantages of such a hybrid $CO_2$-to-organic chemical process include the ability to combine enzymatic capabilities gained through billions of years of evolution in fixing C1 compounds such as $CO_2$, with a wide array of abiotic technologies to power the process such as solar PV, solar thermal, wind, geothermal, hydroelectric, or nuclear, which can be used to generate reducing equivalents needed for carbon fixation, and particularly hydrogen gas or reduced hydrogen atoms or hydride, with established electrolysis technologies from abundant water resources, and particularly non-potable water, salt water, and brine sources. Another potential advantage is the possibility of using syngas or producer gas that is primarily comprised of C1 compounds and hydrogen gas, which represents a low cost carbon source and source of reducing equivalents since it can be readily generated from an array of low cost or waste feedstocks such as lignocellulosic energy crops, crop residues, bagasse, saw dust, forestry residue, food waste, municipal solid waste, sewage, waste carpet, biogas, landfill gas, stranded natural gas, or pet coke, using readily available gasifier, partial oxidation, steam reforming, or pyrolysis technologies known in the art. Microorganisms performing carbon fixation without light can generally be contained in more controlled and protected environments, less prone to water and nutrient loss, contamination, or weather damage, than what can be used for culturing photosynthetic microorganisms such as algae or cyanobacteria. Furthermore an increase in bioreactor capacity can be readily met with vertical rather than horizontal construction, making it potentially far more land efficient than photosynthetic approaches. A hybrid chemical/biological system offers the possibility of a C1-to-organic chemical process that avoids many drawbacks of photosynthesis while retaining the biological capabilities for complex organic synthesis from $CO_2$ and other C1 molecules.

Chemoautotrophic microorganisms are generally microbes that can perform $CO_2$ fixation like in the photosynthetic dark reaction, but which can get the reducing equivalents needed for $CO_2$ fixation from an inorganic external source, rather than having to internally generate them through the photosynthetic light reaction. Carbon fixing biochemical pathways that occur in chemoautotrophs include the reductive tricarboxylic acid cycle, the Calvin-Benson-Bassham cycle, and the Wood-Ljungdahl pathway.

Prior work is known relating to certain applications of chemoautotrophic microorganisms in the capture and conversion of $CO_2$ gas to fixed carbon as well as in the biological conversion of syngas or producer gas to fixed-carbon products. However, many of these approaches have suffered shortcomings that have limited the effectiveness, economic feasibility, practicality and commercial adoption of the described processes. The present invention in certain aspects addresses one or more of the aforementioned shortcomings.

SUMMARY OF THE INVENTION

It is believed that certain embodiments of the present invention provide a bioreactor design that addresses shortcomings present in previous bioreactors and bioprocess designs with respect to growing microbial cultures or performing microbial fermentations that utilize gaseous electron donors, or gaseous electron acceptors, or gaseous carbon sources, or other gaseous nutrients. It is also believed that certain embodiments of the present invention can provide advantages in utilizing oxyhydrogen microorganisms in a bioprocess, and particularly in the chemosynthetic fixation of $CO_2$, or other C1 compounds such as carbon monoxide, under carefully controlled oxygen levels, which may have advantages for the biosynthesis of relatively longer carbon chain organic compounds ($C_5$ and longer). The ability to biologically produce relatively longer chain organic compounds, and particularly relatively hydrophobic longer chain organic compounds in certain embodiments such as triacylglycerols or fatty acids or hydrocarbons, is an important advantage for certain embodiments since the energy densities (energy per unit volume) are generally higher for longer chain hydrophobic organic compounds, and in cases where the said longer chain organic compounds are utilized as transportation biofuels or are converted to transportation biofuels using standard well-known refining processes (e.g. transesterification, hydrotreatment, isomerization, or hydrocracking), the compatibility of such higher energy density biofuels, which in certain embodiments can be biodiesel, renewable diesel, or biojet fuel, with the current transportation fleet and infrastructure is generally greater relative to, for example, the more common shorter chain products of biological syngas conversion processes such as C1 and C2 molecules.

In response to a need in the art that the inventors have recognized in making the invention, which in certain embodiments thereof provides an apparatus for a reactor and particularly a bioreactor the can be used to carry out many different kinds of processes and particularly bioprocesses. The present invention provides in certain embodiments thereof a method and apparatus for efficiently mixing and dissolving gases, including but not limited to H2, CO2, CO, and/or O2, and particularly gases with relatively low solubility in aqueous solution, into a liquid containing microorganisms that consume or otherwise utilize the gases in the production of desired compounds or cell mass components by the microbes in the liquid media. The present invention in certain embodiments thereof also provides a method and apparatus for the capture and recirculation of unconsumed gas that passes through the liquid volume into the headspace such that it is again passed through the liquid volume for further mixing and dissolution of the gas into the liquid. The bioreactor of certain embodiments of the present invention is designed is to entrain and recirculate headspace gas into the biological growth or fermentation media. In some embodiments the ratio of liquid to gas in the entrained fluid approaches 1:1. In some embodiments the apparatus is used to maximize gas usage. In some embodiments the apparatus is used to minimize net influent or effluent gas flows into or from the bioreactor. The mixing of the reactor liquid media with the headspace gas is accomplished through mass flow of liquid through an eductor, or venturi, that creates a pressure reduction in the headspace, thus entraining the gas into the liquid flow path and continuously sparging it through the media.

In some embodiments the reactor of the present invention has one or more of the following features: 1) increases gas transfer efficiency into the aqueous phase; 2) permits the efficient usage of the headspace gas by minimizing venting; 3) allows the ability to break down and recycle foam, before liquid and biomass are lost with the effluent gas stream, therefore minimizing anti-foam usage; 4) is designed to facilitate operation at elevated pressures allowing greater ratios of gas to liquid to be entrained into the media via the eductor, faster kinetics for gas dissolution into solution, and greater thermodynamic driving force in gas-to-liquid conversions such as but not limited to the conversion of syngas into oils.

This method of certain embodiments of the present invention subsumes approaches where (1) all the gases used in the process are mixed together in a single reactor, or (2) gases are spatially separated in fluid connection, where multiple reactors are connected in series or in parallel. Separated reactors in certain embodiments have an advantage of improved safety due to spatial separation of potentially explosive gas mixtures.

In some embodiments of the present invention the use of the bioreactor of the present invention within a novel combined biological and chemical process is described for the capture and conversion of inorganic carbon and/or C1 carbon sources to longer chain organic compounds, and particularly organic compounds with C5 or longer chain lengths. In some embodiments of the present invention the capture and conversion of inorganic carbon and/or C1 carbon sources to longer chain organic compounds, and particularly organic compounds with C5 or longer chain lengths through the use of oxyhydrogen microorganisms for carbon capture and fixation is described. In some embodiments, the process can couple the efficient production of high value organic compounds such as oleochemicals or liquid hydrocarbon fuel with the disposal of waste sources of carbon, or with the capture of $CO_2$ from a waste or flue gas stream, which can generate additional revenue.

The present invention, in certain embodiments, provides compositions and methods for the capture of carbon dioxide from carbon dioxide-containing gas streams and/or atmospheric carbon dioxide or carbon dioxide in dissolved, liquefied or chemically-bound form through a chemical and biological process that utilizes obligate or facultative oxyhydrogen microorganisms, and/or cell extracts containing enzymes from oxyhydrogen microorganisms in one or more carbon fixing process steps carried out within the bioreactor of the present invention.

The present invention, in certain embodiments, provides compositions and methods for the utilization of C1 carbon sources including but not limited to carbon monoxide, methane, methanol, formate, or formic acid, and/or mixtures containing C1 chemicals including but not limited to various syngas compositions or producer gas compositions generated from various gasified, pyrolyzed, or steam-reformed fixed carbon feedstocks, and convert said C1 chemicals into longer chain organic compounds within the bioreactor of the present invention.

The present invention, in certain embodiments, provides compositions and methods for the recovery, processing, and use of the organic compounds produced by chemosynthetic reactions performed by oxyhydrogen microorganisms or hydrogen-oxidizing microorganisms or chemoautotrophic microorganisms to fix inorganic carbon and/or C1 carbon sources into longer chain organic compounds within the bioreactor of the present invention. The present invention, in certain embodiments, provides compositions and methods for the maintenance and control of the oxygen levels in the carbon-fixation environment for the enhanced (e.g., optimal) production of C5 or longer organic compound products through carbon fixation within the bioreactor of the present invention. The present invention, in certain embodiments, provides compositions and methods for the generation, processing and delivery of chemical nutrients needed for carbon-fixation and maintenance of oxyhydrogen or hydrogen-oxidizing or chemoautotrophic cultures, including but not limited to the provision of gaseous electron donors and/or gaseous electron acceptors needed for non-photosynthetic carbon-fixation within the bioreactor of the present invention. The present invention, in certain embodiments, provides compositions and methods for the maintenance of an environment conducive for carbon-fixation, and the recovery and recycling of unused chemical nutrients and process water.

The present invention, in certain embodiments, provides compositions and methods for chemical process steps that occur in series and/or in parallel with the chemosynthetic reaction steps occurring in the bioreactor of the present invention that: convert unrefined raw input chemicals to gaseous electron donors and/or gaseous electron acceptors that are suited for supporting the chemosynthetic carbon fixing step occurring in the bioreactor of the present invention; that convert energy inputs into a chemical form that can be used to drive chemosynthesis, and specifically into chemical energy in the form of gaseous electron donors and/or gaseous electron acceptors that are fed into the bioreactor of the present invention.

The present invention, in certain embodiments, provides compositions and methods for directing inorganic carbon captured from industrial or atmospheric or aquatic sources to the carbon fixation steps of the process occurring in the bioreactor of the present invention under conditions that are suitable to support chemosynthetic carbon fixation by the oxyhydrogen microorganisms or enzymes or hydrogen-oxidizing microorganisms or enzymes or chemoautotrophic microorganisms or enzymes.

The present invention, in certain embodiments, provides compositions and methods for directing C1 chemicals such as carbon monoxide, carbon dioxide, methane, methanol, formate, or formic acid, and/or mixtures containing C1 chemicals including but not limited to various syngas compositions or various producer gas compositions generated from low value or waste sources of carbon and energy such as but not limited to lignocellulosic energy crops, crop residues, bagasse, saw dust, forestry residue, food waste, municipal solid waste, sewage, waste carpet, biogas, landfill gas, stranded natural gas, or pet coke through the gasification, partial oxidation, pyrolysis, or steam reforming of said low value or waste carbon sources, that can be used by an oxyhydrogen microorganism or hydrogen-oxidizing microorganism or carbon monoxide oxidizing microorganism as a carbon source and an energy source for the biosynthesis of longer chain organic chemicals. In certain embodiments, the present invention includes post-processing the output products of the biological carbon fixation steps carried out in the bioreactor of the present invention into a form suitable for storage, shipping, and sale, and/or safe disposal in a manner that results in a net reduction of gaseous $CO_2$ released into the atmosphere, or that results in an oleochemical or oil or fuel product with a lower life cycle greenhouse gas impact than an equivalent chemical derived from fossil petroleum. The present invention, in certain embodiments, provides compositions and methods for the upgrade of a low value or waste material into a finished chemical, fuel, or nutritional product with the bioreactor of the present invention being used in one or more bioprocess steps.

The fully chemical process steps combined with the chemosynthetic carbon fixation steps carried out in the bioreactor of the present invention constitute the overall carbon capture and conversion process for some embodiments of the present invention.

One feature of certain embodiments of the present invention is the inclusion of one or more process steps within a hybrid chemical and biological process for the capture of inorganic carbon and conversion to fixed carbon products, that utilize oxyhydrogen microorganisms or hydrogen-oxidizing microorganisms or chemoautotrophic microorganisms and/or enzymes from said microorganisms as a biocatalyst for the fixation of carbon dioxide in carbon dioxide-containing gas streams or the atmosphere or water and/or dissolved or solid forms of inorganic carbon, into organic compounds where said fixation of inorganic carbon and conversion of organic compounds occurs within the bioreactor of the present invention. In some such embodiments carbon dioxide containing flue gas, or process gas, or air, or inorganic carbon in solution as dissolved carbon dioxide, carbonate ion, or bicarbonate ion including aqueous solutions such as sea water, or inorganic carbon in solid phases such as but not limited to carbonates and bicarbonates, is pumped or otherwise added to one or more bioreactors of the present invention containing nutrient media and oxyhydrogen microorganisms or hydrogen oxidizing microorganisms or chemoautotrophic microorganisms. In some such cases oxyhydrogen microorganisms or hydrogen-oxidizing microorganisms or chemoautotrophic microorganisms perform chemosynthesis to fix inorganic carbon into organic compounds within the bioreactor of the present invention using the chemical energy stored in molecular hydrogen and/or valence or conduction electrons in solid state electrode materials and/or one or more of the following list of electron donors pumped or otherwise provided to the nutrient media including but not limited to: ammonia; ammonium; carbon monoxide; dithionite; elemental sulfur; hydrocarbons; metabisulfites; nitric oxide; nitrites; sulfates such as thiosulfates including but not limited to sodium thiosulfate ($Na_2S_2O_3$) or calcium thiosulfate ($CaS_2O_3$); sulfides such as hydrogen sulfide; sulfites; thionate; thionite; transition metals or their sulfides, oxides, chalcogenides, halides, hydroxides, oxyhydroxides, sulfates, or carbonates, in soluble or solid phases. The electron donors can be oxidized by electron acceptors in the chemosynthetic reaction. In some embodiments of the present invention oxygen is used as an electron acceptor at the chemosynthetic reaction step or steps, which occurs in the bioreactor of the present invention. In some embodiment of the present invention one or more of the following electron acceptors are used at the chemosynthetic reaction step or steps occurring in the bioreactor of the present invention: carbon dioxide, ferric iron or other transition metal ions, nitrates, nitrites, oxygen, or holes in solid state electrode materials; where the oxygen level may be aerobic in some embodiments, microaerobic in other embodiments, or anaerobic in other embodiments, as understood in the art and science of fermentation.

One feature of certain embodiments of the present invention is the inclusion of one or more process steps within a hybrid chemical and biological process for the biological conversion of C1 carbon sources within the bioreactor of the present invention including but not limited to carbon monoxide, methane, methanol, formate, or formic acid, and/or mixtures containing C1 chemicals including but not limited to various syngas compositions or producer gas compositions where said C1 carbon sources are generated from various gasified, pyrolyzed, partially oxidized, or steam-reformed fixed carbon feedstocks, where the biological conversion within the bioreactor of the present invention utilizes oxyhydrogen microorganisms and/or enzymes from oxyhydrogen microorganisms as a biocatalyst for the conversion of C1 chemicals into longer chain organic chemicals i.e. C2 or longer and particularly C5 or longer carbon chain molecules. In some embodiments C1 containing syngas, or producer gas or process gas, or industrial tail gas, or C1 chemicals in a pure liquid form or dissolved in solution is pumped or otherwise added to the bioreactor of the present invention containing nutrient media and oxyhydrogen microorganisms or hydrogen-oxidizing microorganisms, or carbon-monoxide oxidizing microorganisms, or chemoautotrophic microorganisms. In some such cases oxyhydrogen microorganisms perform biochemical synthesis to elongate C1 chemicals into longer carbon chain organic chemicals using the chemical energy stored in the C1 chemical, and/or molecular hydrogen and/or valence or conduction electrons in solid state electrode materials and/or one or more of the following list of electron donors pumped or otherwise provided to the nutrient media including but not limited to: ammonia; ammonium; carbon monoxide; dithionite; elemental sulfur; hydrocarbons; metabisulfites; nitric oxide; nitrites; sulfates such as thiosulfates including but not limited to sodium thiosulfate ($Na_2S_2O_3$) or calcium thiosulfate ($CaS_2O_3$); sulfides such as hydrogen sulfide; sulfites; thionate; thionite; transition metals or their sulfides, oxides, chalcogenides, halides, hydroxides, oxyhydroxides, sulfates, or carbonates, in soluble or solid phases. The electron donors can be oxidized by electron acceptors in a chemosynthetic reaction. Electron acceptors that may be used at this reaction step include oxygen and/or other electron acceptors including but not limited to one or more of the following: carbon dioxide, ferric iron or other transition metal ions, nitrates, nitrites, oxygen, or holes in solid state electrode materials.

In certain embodiments of the present invention the chemosynthetic reaction step or steps of the process whereby carbon dioxide and/or inorganic carbon is fixed into organic carbon in the form of organic compounds and biomass and/or the reaction steps converting C1 chemicals to longer chain organic chemicals whereby a C1 chemical such as but not limited to carbon monoxide, methane, methanol, formate, or formic acid, and/or mixtures containing C1 chemicals including but not limited to various syngas compositions or producer gas compositions generated from various gasified, pyrolyzed, partially oxidized, or steam-reformed fixed-carbon or methane feedstocks, are biochemically converted within the bioreactor of the present invention into longer chain organic chemicals i.e. C2 or longer and particularly C5 or longer carbon chain molecules, where said biological conversion can be performed in aerobic, microaerobic, anoxic, or anaerobic conditions maintained within the bioreactor in the present invention.

The oxygen level is controlled inside the bioreactor in some embodiments of the current invention so that the production of targeted organic compounds by oxyhydrogen microorganisms through carbon-fixation in the bioreactor of the present invention is controlled (e.g., optimized). One objective of controlling oxygen levels is to control (e.g., optimize) the intracellular Adenosine Triphosphate (ATP) concentration through the cellular reduction of oxygen and production of ATP by oxidative phosphorylation, while simultaneously keeping the environment sufficiently reducing so that a high ratio of NADH (or NADPH) to NAD (or NADP) is also maintained.

In some embodiments of the present invention a hydrogen-oxidizing or carbon-monoxide oxidizing microorganism having greater tolerance for oxygen than a strictly anaerobic acetogenic or methanogenic hydrogen-oxidizing or carbon-monoxide oxidizing microorganism is utilized in a chemosynthetic reaction step or steps occurring in the bioreactor of the present invention. In some embodiments that hydrogen-oxidizing or carbon-monoxide oxidizing microorganism is an oxyhydrogen microorganism. In some embodiments the microorganism is a cell of the class Actinobacteria. In some embodiments, the microorganism is strain of the suborder corynebacterineae (corynebacterium, gordoniaceae, mycobacteriaceae and nocardiaceae). In some embodiments the microorganisms is a cell of the family of Nocardiaceae. In some embodiments the microorganism or microorganisms are drawn from one or more of the following classifications: *Corynebacterium, Gordonia, Rhodococcus, Mycobacterium* and *Tsukamurella*. In some embodiments, the microorganism is a cell of the genus *Rhodococcus*. In some embodiments the cell is a strain of the species *Rhodococcus* sp., *Rhodococcus opacus, Rhodococcus aurantiacus; Rhodococcus baikonurensis; Rhodococcus boritolerans; Rhodococcus equi; Rhodococcus coprophilus; Rhodococcus corynebacterioides; Nocardia corynebacterioides* (synonym: *Nocardia corynebacterioides*); *Rhodococcus erythropolis; Rhodococcus fascians; Rhodococcus globerulus; Rhodococcus gordoniae; Rhodococcus jostii Rhodococcus koreensis; Rhodococcus kroppenstedtii; Rhodococcus maanshanensis; Rhodococcus marinonascens; Rhodococcus opacus; Rhodococcus percolatus; Rhodococcus phenolicus; Rhodococcus polyvorum; Rhodococcus pyridinivorans; Rhodococcus rhodochrous; Rhodococcus rhodnii;* (synonym: *Nocardia rhodnii*); *Rhodococcus ruber* (synonym: *Streptothrix rubra*); *Rhodococcus* sp. RHA1; *Rhodococcus triatomae; Rhodococcus tukisamuensis; Rhodococcus wratislaviensis* (synonym: *Tsukamurella wratislaviensis*); *Rhodococcus yunnanensis; Rhodococcus zopfii*. In some embodiments, the microorganism is strain *Rhodococcus opacus* DSM number 43205 or 43206. In some embodiments, the microorganism is strain *Rhodococcus* sp. DSM number 3346. In some embodiments, the microorganism is a strain within the family burkholderiaceae. In some embodiments the microorganisms is a strain within the genus *Cupriavidus* or *Ralstonia*. In some embodiments the microorganism is a strain of the species *Cupriavidus necator*. In some embodiments the microorganism is the strain *Cupriavidus necator* DSM number 531 or 541.

An additional feature of certain embodiments of the present invention regards the source, production, or recycling of the electron donors used by oxyhydrogen microorganisms or hydrogen-oxidizing microorganisms or carbon-monoxide oxidizing microorganisms or chemoautotrophic microorganisms to fix carbon dioxide into organic compounds and/or to synthesize longer carbon chain organic molecules from C1 chemicals. The electron donors used for carbon dioxide capture and carbon fixation can be produced or recycled in certain embodiments of the present invention electrochemically or thermochemically using power from a number of different renewable and/or low carbon emission energy technologies including but not limited to: photovoltaics, solar thermal, wind power, hydroelectric, nuclear, geothermal, enhanced geothermal, ocean thermal, ocean wave power, tidal power.

An additional feature of certain embodiments of the present invention regards cultivating genetically modified microbial cultures that utilize gaseous electron donors, electron acceptors, carbon sources, or other nutrients within the bioreactor of the present invention. In some embodiments that modified microorganisms is an oxyhydrogen microorganism or hydrogen-oxidizing microorganism or carbon monoxide oxidizing microorganism or a chemoautotrophic microorganism. In some embodiments the said microorganism has been modified through artificial means including but not limited to accelerated mutagenesis (e.g. using ultraviolet light or chemical treatments), genetic engineering or modification, hybridization, synthetic biology or traditional selective breeding.

Also described are compositions and methods incorporating the bioreactor of the present invention that reduce the hazards of performing gas cultivations or fermentations that utilize mixtures of hydrogen and oxygen within the invented process.

Also described are process steps in certain embodiments of the present invention for the recovery and further finishing of useful chemicals or oils or oleochemicals produced both by biological carbon fixation steps in certain embodiments of the process Other advantages and novel features of the present invention will become apparent from the following detailed description of various non-limiting embodiments of the invention when considered in conjunction with the accompanying figures. All publications, patent applications and patents mentioned in the text are incorporated by reference in their entirety. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Description of a Reactor Example

Figure 1:
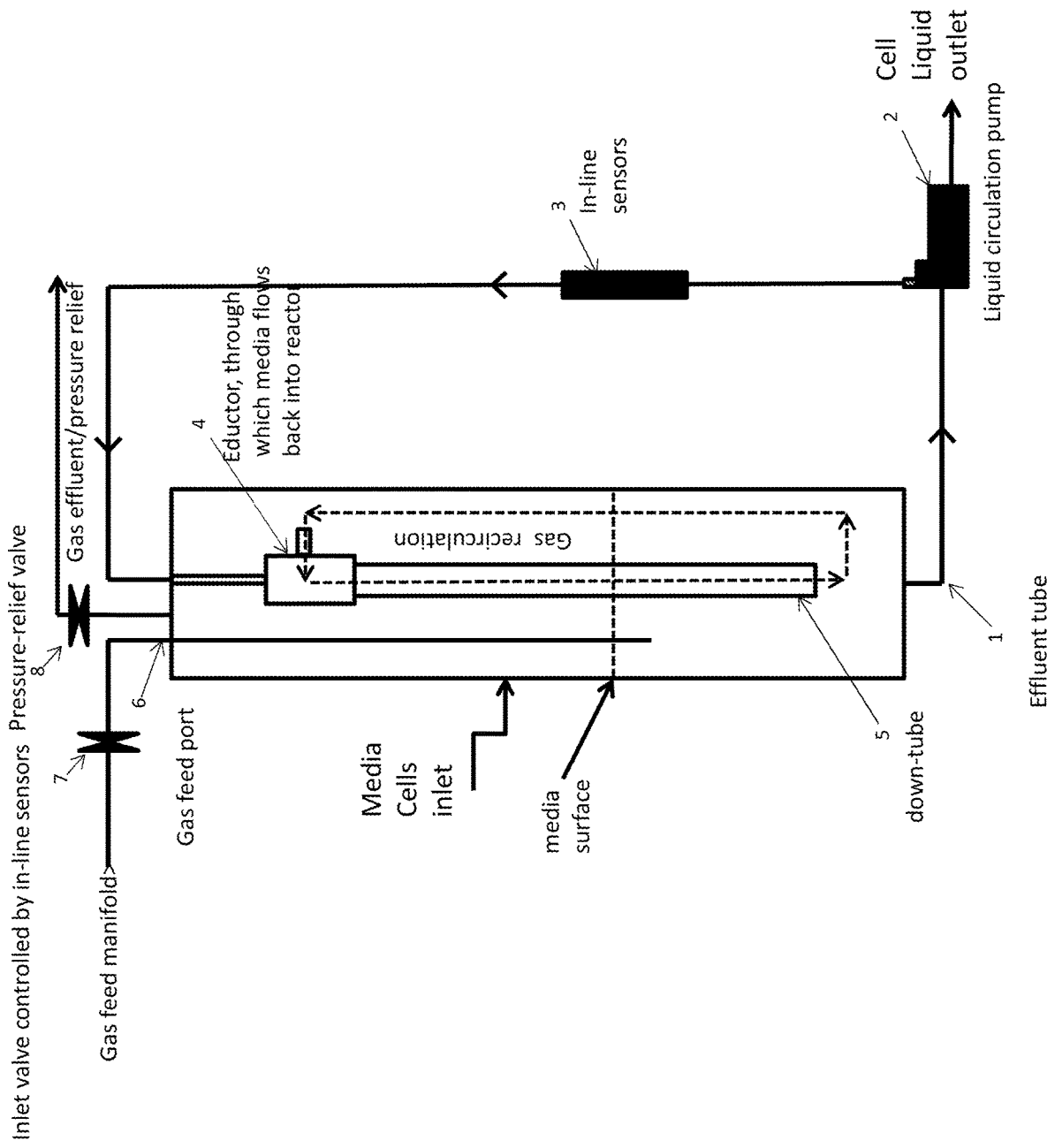
FIG. 1 is a diagram of a non-limiting embodiment of the present invention as reduced to practice. Media is circulated from the reactor via the effluent tube (1) by the circulating pump (2) and through various in-line sensors (3) that measure aqueous phase parameters (i.e.—pH, dissolved gas composition, temperature, etc.). Media flows back into the reactor through the eductor (4) where headspace gases are entrained into the liquid stream and enter the reactor through the down-tube (5). Gases enter the reactor through the gas feed port (6) where feedback from the in-line sensors (3) are used to control the inlet valve (7) as to the mass and composition gases to be added to the reactor. A pressure relief valve (8) is used to control the total pressure of the system and allow the venting of gases that may be required if the concentration of inert constituents becomes too high. In this way gas components may be added at an equivalent rate to their consumption with minimal venting.

FIG. 1 shows a prototype reactor for one non-limiting embodiment given as an example of the present invention. A key to its function is the efficient and thorough mixing of the gases from headspace back into the aqueous phase as indicated by the formation of an opaque liquid (that is completely filled with tiny bubbles from the thorough mixing) occurring in the reactor tube. In some embodiments this opaqueness can be visually confirmed with a reactor tube constructed out of a transparent material such as but not limited to a transparent high strength plastic.

The apparatus of one possible non-limiting embodiment of the bioreactor of the present invention has been constructed such that the following are implemented. See FIG. 1 for a schematic diagram of the prototype. This prototype is a non-limiting embodiment of the present invention that is described by way of example:
1) Gas is supplied to the reactor via the gas feed manifold; gas flow is controlled by an inlet valve (7), which is regulated by in-line sensors which detect the aqueous phase parameters, including pH, dissolved gas composition, temperature, etc. Gas enters the reactor vessel via the gas feed port (6) and is injected below the surface of the media. In some embodiments the gas is a mixture of energy and carbon source for the growth of chemoautotrophic organisms, such as but not limited to of H2 and CO2.
2) Gas exits the reactor via a pressure-relief valve (8) when pressure reaches a maximum set point; however, this approach is designed to maximize the usage of gas through recirculation through the liquid media so that microbes in the media layer use up to 100% of gas in production of cellular components and/or secreted compounds (e.g., lipids or specialty chemicals such as hydroxylated fatty acids).
3) In some embodiments the reactor vessel is intended to run with both a liquid (media and microbes) phase at the bottom and with gas (such as but not limited to H2 and CO2) at the top (headspace).
4) An eductor (4) permits the flow of media back into the liquid media portion of the reactor through a downtube (5). The eductor or venturi creates a decrease in pressure in the headspace, thus entraining the gas into the liquid flow path and continuously sparging it through the media.
5) Media effluent is taken from the media layer through an effluent tube (1), then pumped via a liquid circulation pump (2), through a tube containing in-line sensors (3), back into the reactor via the eductor.
6) A tee in the circulation path leads to a valved-luer fitting for inlet and outlet lines for supply and sampling/harvest.
7) Reactor dimensions can be readily modified in different embodiments of the present invention, including height, which can facilitate the attainment of higher internal pressures.

Description of Some Invention Embodiments

In some embodiments in-line sensors utilized in the bioreactor as diagrammed in FIG. 1 consist of devices which can measure parameters including but not limited to pH (e.g., pH meter), gas composition/content (e.g., GC or gas chromatograph), cell density (OD or Optical Density), temperature, pressure, liquid flow rate, redox potential or dissolved oxygen (DO electrical probes), and detectors for nutrients: nitrogen content (e.g., ammonium chloride or ammonium hydroxide) and other nutrients.

In some embodiments in-line sensors in the bioreactor feed data back to a controlling computer (central processing unit), which is used to determine how much gas feed stock should be added to the reactor via the gas, feed manifold and inlet valve. When the computer determines that gas levels have dropped below a certain pre-set level, the feed levels of gas are increased. In some embodiments the gases being fed into the system are CO2 and H2. In some embodiments multiple gas feeds include oxygen, syngas or syngas components, each differentially controlled. In some embodiments cell density feedback is connected to rate of harvest from the system, in a continuous fermentation or cultivation process—if cell density surpasses a certain set point, removal of cell mass from the system is increased; if cell density drops below another set point, removal of cell mass from the system is decreased. In some embodiments pH is controlled by addition of acid or base for pH control to maintain a target pH. In some embodiments temperature is controlled by heating or cooling. In some embodiments a pressure sensor feeds back to gas flow in order to increase or decrease pressure or maintain a target pressure. In some embodiments liquid flow rate feeds back to the liquid pump. In some embodiments redox potential feeds back to the flow rates of H2, CO2, syngas, or O2. In some embodiments dissolved oxygen (DO) feeds back to rates of flow of O2, H2, CO2, or syngas. In some embodiments a detector for nutrient levels feeds back to a nutrient feed controller.

In some embodiments Gas Chromatography (GC) or High Pressure Liquid Chromatography (HPLC) is used for testing any compound concentrations in the media and re-direct stream that may be of interest for extraction or filtering or recovery (e.g., with secreted compounds such as but not limited to hydrocarbons, fatty alcohols, fatty acids, organic acids or alcohols) from the cell mass and/or the media. For example, GC or HPLC may be used to detect hydrocarbons or fatty alcohols. In some embodiments a liquid/liquid separation is performed on cell free media, post-harvest to recover a desired product in the media. In some embodiments lipids are extracted from the cell mass using one of the standard methods known in the art including but not limited to solvent extraction. In some embodiments the remainder of the media following the extraction of product is recycled back to the reactor. In some embodiments a filter with less than 0.2 um pore size is used to remove cells from the media. In other embodiments a filter with less than 0.45 um pore size is used to remove cells from the media. In some embodiments a high-shear alignment is used to keep the filter clear of cell mass.

In some embodiments detection of lipid content is used to determine status of lipid generation and redirect flow of cells out of the system for harvest when a certain level of lipids is reached. In some embodiments said detection of lipid is an optical absorption technique, which uses Nile Red lipophilic dye.

In some embodiments there is testing of the cell state in the reactor such that an optimal time to alter reaction conditions or stop the reaction may be identified. In some embodiments a continuous process or fermentation is maintained at one point in the cell cycle; with cell density, nutrients, etc. controlled so that steady state is maintained. In some embodiments a batch process is performed, and in some embodiments the cell mass or other biosynthesized product is harvested when product composition is at its maximum density, for example In some embodiments monitoring of reaction conditions is electronically communicated to an outside website or a signal controller or human manufacturing personnel. In some embodiments determination of reaction completion is accomplished through monitoring various bioprocess parameters. In some embodiments that are run in batch mode or sequential batch mode, parameters including cell density or optical density (OD) used as a proxy for cell density, dissolved oxygen, nitrogen levels and/or a timeline are used to determine reaction completion. In some embodiments these readings can provide indirect evidence of the storage of lipids. In some embodiments pH is used to monitor change from logarithmic growth phase to storage phase. In some embodiments reactor design parameters such as liquid column height are utilized to attain higher internal pressures.

Description of the Combinations of in Series Reactor Pairs

In some embodiments of the present invention, two or more reactors are connected in series, such that the outflow from reactor 1 feeds into reactor 2. In some embodiments of the present invention the output from reactor 2 is then fed into the next reactor in the series. In some embodiments of the present invention two reactors are connected in series, such that the outflow from reactor 1 feeds into reactor 2 and the outflow of reactor 2 is fed back into reactor 1. See FIGS. 2 and 3 for examples of two reactors joined in series.

In some embodiments, the reactors can contain different combinations of gases; for example, in one embodiment having a two-reactor system, one reactor can contain electron donor gases (e.g., H2-rich or CO-rich side), and the other reactor can contain electron acceptor gases (e.g. O2-rich side). In some embodiments with reactors in series, fuel gases (e.g. H2 or CO) can be kept from mixing with air or O2, thus avoiding dangerous flammable or explosive gas mixes in the bioreactor headspace, or to prevent mixing fuel gases with N2 from air, which could otherwise build up with gas recirculation and increase requirements for headspace gases to be purged. In other embodiments, spatial separation benefits cell growth phase (e.g., spatial separation of cultures is based on the age of the culture). For example, in one embodiment a continuous steady state of maximum cell mass productivity is maintained in the first bioreactor, where the culture is maintained in log phase growth, and in the next reactor a nitrogen source-poor (e.g. ammonium deficient) environment is maintained, in order to optimize production of lipids. In this embodiment the cells flow from the bioreactor maintained for maximum cell mass productivity to the bioreactor with ammonium deficiency where the cells in stationary phase accumulate lipid.

In some embodiments of the present invention there is a "plug flow" system, where each individual reactor connected in series is maintained a different stage of cellular growth phase, where cells, broth, or cell+broth are fed into each respective reactor at the nutrient levels and gas mixes specific to that stage of the growth.

In some embodiments of the present invention, the interfaces between reactors permit transfer of different effluents. In some embodiments the cells and broth are transferred between bioreactors. This particular case represents a plug flow between reactors. In some embodiments of the present invention where a plug flow occurs between reactors, the conditions change from reactor to reactor due to consumption of a certain nutrient by the microorganisms or the production of a product or co-product or waste product. For example in one type of embodiment the media in a subsequent reactors connected become depleted of a nitrogen source such as ammonium ion due to the uptake and assimilation of the ammonium by the microorganism. In some embodiments of the present invention this depletion of nitrogen-source induces lipid production and storage in the microorganism. In some embodiments of the present invention there is a cells-only transfer between bioreactors. For example, in certain embodiments cells are grown in the first reactor, which contains an environment, rich in a nitrogen source such as ammonium ion. In such embodiments concentrated cells (i.e. largely or completely separated from the liquid broth) are transferred from the first reactor to a second reactor, which is poor in a nitrogen source such as ammonium ion. In some of these embodiments lipid accumulation occurs in the bioreactor that has low and zero quantities of nitrogen source.

In some embodiments of the present invention there is a broth only transfer between bioreactors. For example in certain embodiments initial growth with one organism produces a substance or compound that is dissolved or mixed in the media, and the largely or completely cell-free media containing the dissolved or mixed constituent (e.g., acetic acid or other compounds produced by anaerobic respiration in the first reactor) is transferred from the first reactor to a second reactor, where a second organism consumes and/or processes the dissolved or mixed constituent. For example in one embodiment a microorganism in the second bioreactor synthesizes fatty acids or triacylglycerols from acetic acid produced in the first reactor.

For certain embodiments where two or more reactors are connected in series (See FIGS. 2 and 3), where each reactor has a different gas inlet, if Reactor 1 receives an influx of gas A (e.g., O2 or air), then the media in reactor 1 will reach the desired or nominal dissolved concentration of oxygen, and other gases—gas B (e.g., CO2/H2)—will drop down to a relatively low concentration in solution. When the cells, cells+broth or broth-only are then transferred to the next reactor, the transferred liquid or cells will have reached a desired or nominal concentration of gas A (e.g. oxygen) and a relatively low concentration of gas B (e.g. CO2/H2). When cells enter reactor 2, they will be exposed to a high concentration of gas B (e.g. CO2/H2) and dissolved concentrations of gas B (e.g. CO2/H2) will increase to desired or nominal levels, while the dissolved concentration of gas A (e.g. O2) will drop. Recycling back to reactor 1 will repeat the increase in dissolved gas A (e.g. O2) and decrease in dissolved gas B (e.g. CO2/H2). In some embodiments that exposure to concentrations of different gases in different reactors will be gradual since the recycling of headspace gas in the reactors can cause a gas not directly supplied to that reactor to drop gradually. See section on gas saturation curves below.

In another embodiment, more than two reactors can be used to infuse more than two gases or combinations of gases in fixed series, therefore allowing the cells in each successive reactor to be exposed to higher concentrations of a new combination of gas added to that reactor. In some embodiments the increase and drop off in dissolved concentrations of these gases will be gradual due to the recycling of the gases from headspace in the reactors.

Description of the Combinations of in Parallel Reactor Pairs

In some embodiments, the reactors are connected in parallel stages with mixing of cells and media in separate mixing vessels between stages. This design differs from that of the in series reactors since in the in-parallel system, gases are supplied to different reactors holding bifurcated branches of the process stream. When the two different effluent streams are mixed, the concentrations of the two different inlet gases (from the separate reactors of the previous stage) are equilibrated by the mixing of the liquids in a mixer (CSTR). See FIGS. 4 and 5.

In some embodiments this approach allows the cells to be exposed to one gas or gas mix (e.g., CO2/H2) in a reactor at one stage (e.g., reactor 1B) and other cells to be exposed to another gas or gas mix (e.g., O2 or air) in a reactor at another stage (e.g., reactor 1A) for a certain length of time. When these cells/media are pumped out into a single reactor and mixed, then all the cells and broth are mixed and dissolved gases B (e.g. CO2/H2) and gases A (e.g. O2) equilibrate at a lower concentration based on the new total volume and then gradually drop as cells use the gases. This approach permits the cells to be separately exposed to different gas streams, and then to the dissolved part of both gas streams combined. The homogeneous cell mixture is then separated and distributed into the two reactors at the next stage, again exposing one reactor to one gas stream and the other reactor to the other gas stream.

In various embodiments this approach may be repeated in different stages, with different combinations of gases supplied to different reactors at any stage. There may also be two or more parallel reactors at each stage.

Figure 4:
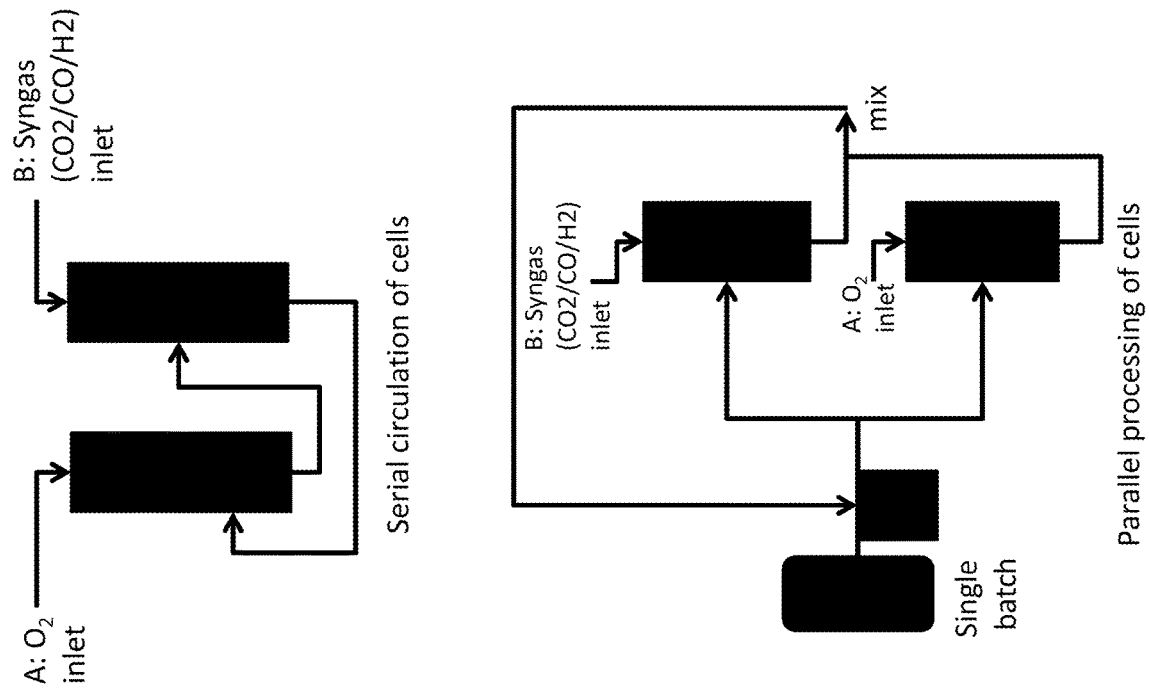
FIG. 4 compares two reactors connected in series with pairs of reactors connected in parallel. In certain embodiments each reactor may have different compositions of gas delivered to it. In the series pair, the effluent (cells-only, media-only, or cells+media) is sent from one reactor to the next. In the parallel pairs, the effluent is mixed, then distributed into a pair of reactors where different portions may be exposed to two different gas mixtures in parallel, then the effluent is remixed and then re-distributed. In both cases, the concentration of respective gases dissolved into solution can vary over time in certain embodiments.
Figure 5:
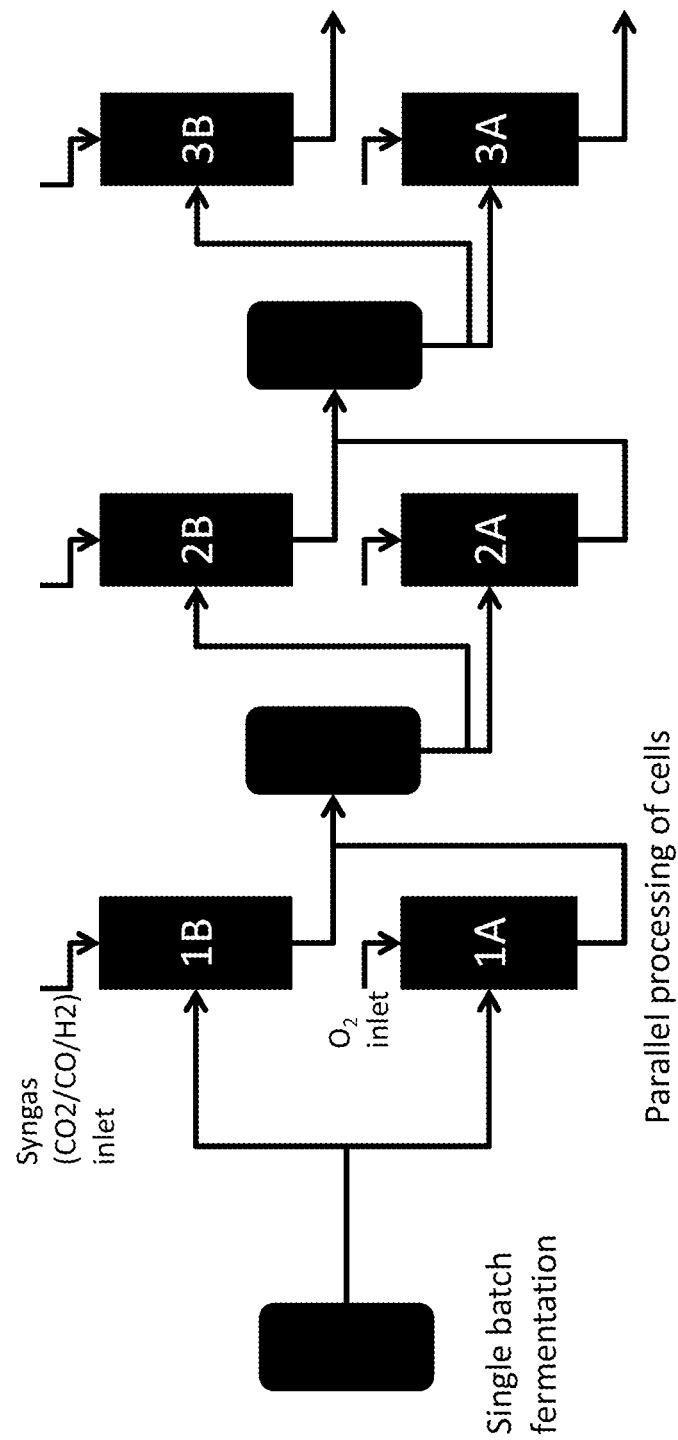
FIG. 5 is diagram of successive pairs of parallel reactors, which include recombining and mixing stations between distribution of effluent into separate reactors at each stage.

As per FIG. 4, the in-series and in-parallel approaches treat the cell exposure to gases differently, producing different effects.

The two systems have in common the concept that, in certain embodiments, each reactor has different compositions of gas delivered. In the series pair, the effluent (cells-only, media-only, or cells+media) is sent from reactor to the next. In the parallel pairs, the effluent is mixed, then distributed into a pair of reactors where different portions are exposed to two different gas mixtures in parallel, then the effluent is remixed and then re-distributed. In both cases, the dissolution (ramp up and ramp down) of gases varies over a period of time, as per the gas transfer experiment described in the text.

Gas Transfer Experiments

Figure 6:
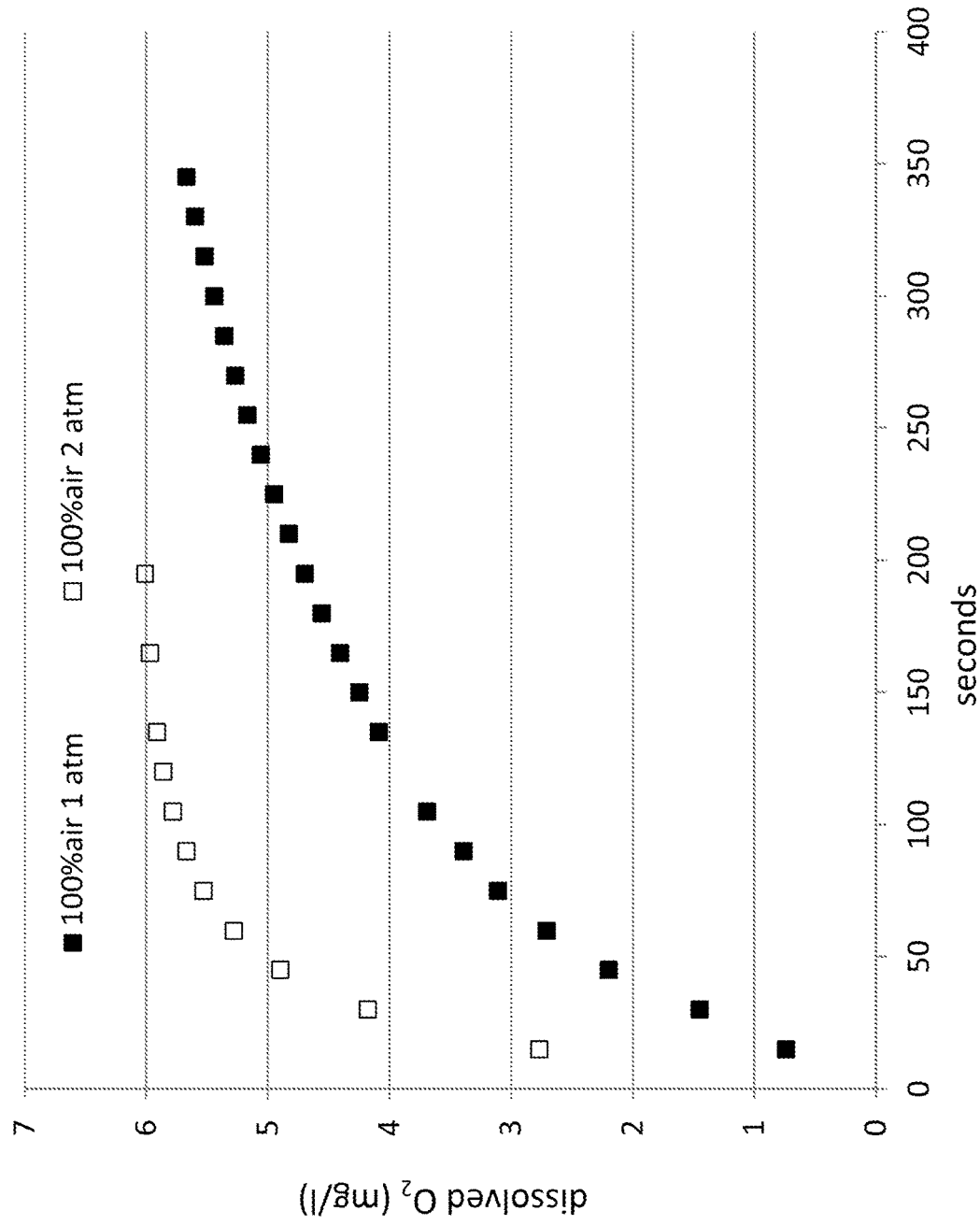
FIG. 6 This set of experiments demonstrates the rate of saturation of liquid phase with O2 over time (dissolved O2 (mg/L) vs. time (sec)) at two different reactor pressures within a bioreactor designed according to the present invention. At 1 atmosphere pressure of air, dissolved O2 goes from 0.0 mg/L at t=0 to 5.67 mg/L at t=345 s. At 2 atmospheres air pressure, the dissolved O2 saturates at 6 mg/L at t=195 s. In each case, the headspace was first purged with 100% N2 until the dissolved O2 was undetectable, then the liquid circulation pump was shut off and the headspace was switched to 100% air at 100 ml/min for 10 minutes. The liquid circulation pump was then restarted and the dissolved O2 increase was measured for several minutes.

A set of experiments were run in the prototype reactor, which is one non-limiting embodiment of the present invention given as an example, in order to test the saturation of gases in the liquid phase of the reactor in this particular case. First the liquid of the bioreactor was sparged with nitrogen N2 in order to drive out all oxygen, then the liquid was bubbled with air at two different pressures: 1 atmosphere or 2 atmospheres. Dissolved oxygen O2 was measured in 15 second intervals. For up to 360 seconds. As per FIG. 6, this set of experiments demonstrates the gradual saturation of liquid phase with O2 over time (dissolved O2 (mg/L) vs. time (sec)) at two different reactor pressures. At 1 atmosphere pressure of air, dissolved O2 goes from 0 to 5.67 mg/L t=345 s. At 2 atmospheres air pressure, the dissolved O2 saturates at 6 mg/L at t=195 s. This illustrates how greater pressure leads to faster saturation kinetics in our prototype system. In certain embodiments of the present invention increased gas pressure is used to enhance gas dissolution.

Embodiments Using Syngas

In some embodiments of the present invention that utilize syngas or producer gas as a source of carbon and/or electron donors, the syngas or producer gas may be produced by a variety of means including but not limited to gasification, pyrolysis, partial oxidation, or steam-reforming of feedstocks such as but not limited to municipal waste, black liquor, agricultural waste, wood waste, stranded natural gas, biogas, sour gas, methane hydrates, tires, sewage, manure, straw, and low value, highly lignocellulosic biomass in general, pet coke and the syngas or producer may be composed of a range of gases that generally includes carbon monoxide and/or hydrogen and carbon dioxide in varying ratios depending on syngas or producer gas sources and any scrubbing or pre-processing of input gas (carbon and electron donor source) as is known in the art and science of syngas and producer gas processing.

Syngas or producer gas may be generated from a variety of sources and be composed of a range of gases. In certain embodiments of the present invention syngas or producer gas can be fed into the bioreactor containing chemoautotrophic bacteria, where the syngas or producer gas can be subjected to different levels of scrubbing (e.g., removing CO2 and impurities) and modification (e.g., increasing H2 through the water-gas shift reaction) prior to being fed into the bioreactor containing microorganisms depending on the embodiment of the invention. In these particular embodiments microorganisms use the syngas or producer gas as a carbon or energy source, or in some way bioprocess the syngas.

There are a wide range of syngas and producer gas compositions depending on the feedstock, type of process through which it has been generated (e.g. gasifier, partial oxidizer, pyrolyzer, or steam reformer) whether the syngas generation process is air blown or O2 blown, the amount of steam utilized, and whether heat driving the process is generated directly within the reactor (e.g. combustion reactions occurring within the same reactor that generates syngas such as direct gasification) or is provided indirectly to the reactor generating syngas through a heat transfer system (e.g. combustion reactions occurring in a different reactor from that which generates syngas such as indirect gasification). The bioreactor and microorganisms of the present invention can be adapted to a wide range of syngas compositions. By way of example and not intending to limit, in any way, the scope of this invention a typical unprocessed gas composition resulting from the gasification of various biomass or waste lignocellulosic feedstocks would be a H2:CO ratio of ~1 and a CO2:CO ratio of ~0.6 (syngas or producer gas from steam reforming a natural gas or biogas source or other methane-rich source would have a higher H2:CO ratio). For a syngas produced from a direct O2 blown gasifier or an indirect gasifier this would correspond to volume % of each non-condensable gas of about 39% H2, 39% CO, and 22% CO2. For a producer gas from an air blown direct gasifier this gas mix would be diluted by 50-70% N2. In some embodiments of the present invention the process is designed for these types of syngas or producer gas mixes which are centered on these common proportions of H2:CO:CO2 associated with the gasification of biomass or waste lignocellulosic feedstocks. In some embodiments of the present invention producer gas from an air blown gasifier is used in preference to syngas from an O2 blown gasifier in order to lower the capital costs of the gasifier, and to remove the capital and operational costs of an air separation unit associated with O2 blown gasification. In some embodiments of the present invention syngas from an O2 blow gasifier is used in preference to producer gas from an air-blown gasifier in order to reduce gas volume and thus lower capital cost for piping and downstream reactor sizes, and to reduce the steps added to the process to mitigate a build up of inert gas in the system (e.g. N2) and minimize any losses of energy sources (i.e. H2 and CO) due to purging built up inert gas. Another large constituent of syngas, depending on the syngas generation process and feedstock, can be water vapor, which will condense into the media in the bioreactor. In some embodiments the water product of the syngas or producer gas generation process is utilized to help meet overall process water demand in the present invention.

In some embodiments a chemical water gas shift step is included in the process prior to the introduction of the syngas or producer gas into the bioreactor, which produces an increase the H2:CO ratio of the syngas or producer gas. The water gas shift is a very well established process step used routinely in the largest chemical processes such as at oil refineries to produce H2 for hydrocracking and isomerization, as well as at ammonia synthesis plants for the production of H2 for the hydrogenation of N2.

In some embodiments the bioreactor comprises a platform that can be readily adapted to a wide range of syngas compositions that might arise in various scenarios of feedstock/syngas generation (e.g. gasifier type) combinations. H2:CO ratios can conceivably range from 0.4 to 6.2 and CO2:CO ratios range from 0 to 8.6 depending on feedstock/syngas generation (e.g. gasifier type) combinations.

In addition to the primary constituents of syngas (H2, CO, CO2, and N2 in the case of producer gas) in some embodiments the microorganism that utilize or process the syngas have a high tolerance and/or use by the microbe of various impurities commonly found in syngas.

In some embodiments the impurity in syngas that is utilized by the microorganisms is methane or CH4. The volume fraction of CH4 in syngas can vary from 0 to 10%, depending on process/feedstock but generally is below 1%.

In some embodiments the impurities in syngas or producer that are utilized and/or tolerated by the microorganisms include H2S, C2H6, C2H4, C6H6, NH3, tar, COS, Methylene, O2, and particulates. All such impurities combined generally will not comprise more than 4% of the syngas or producer gas stream and usually comprise only about 0-0.5% combined of the syngas or producer gas stream. Individually any of these impurities can range from 0 to 2% depending on the process/feedstock. When any of these syngas or producer gas impurities prove to be problematic, there are standard, well-established process steps for removing them from a syngas or producer gas stream already used on a huge scale in the petrochemical, ammonia, and natural gas industries. In some embodiments of the present invention these standard, well-established process steps used on a huge scale in the petrochemical, ammonia, and natural gas industries (e.g. tar or H2S removal) are used for removing certain impurities (e.g. tar or H2S) from a syngas or producer gas stream.

In some embodiments O2 or air is added to the bioreactor system in a separate stream from the syngas in an amount determined by the DO monitored in the bioreactor. In some embodiments the DO will generally be kept below 2 ppm. Some such embodiments utilize an oxyhydrogen microorganism as a biocatalyst in the bioreactor of the present invention.

The present invention provides, in certain embodiments, compositions and methods for the capture and fixation of carbon dioxide from carbon dioxide-containing gas streams and/or atmospheric carbon dioxide or carbon dioxide in liquefied or chemically-bound form through a chemical and biological process that utilizes obligate or facultative oxyhydrogen, or hydrogen-oxidizing, or carbon monoxide-oxidizing, or chemoautotrophic microorganisms, and/or cell extracts containing enzymes from oxyhydrogen, or hydrogen-oxidizing, or carbon monoxide-oxidizing, or chemoautotrophic microorganisms in one or more process steps where the said microorganisms are grown or maintained in bioreactors of the present invention. Cell extracts include but are not limited to: a lysate, extract, fraction or purified product exhibiting chemosynthetic or biosynthetic enzyme activity that can be created by standard methods from oxyhydrogen, or hydrogen-oxidizing, or carbon monoxide-oxidizing, or chemoautotrophic microorganisms. In addition the present invention, in certain embodiments, provides compositions and methods for the recovery, processing, and use of the chemical products of chemosynthetic reaction step or steps performed by oxyhydrogen, or hydrogen-oxidizing, or carbon monoxide-oxidizing, or chemoautotrophic microorganisms to fix inorganic carbon into organic compounds and/or biosynthetic reaction step or steps performed by oxyhydrogen, or hydrogen-oxidizing, or carbon monoxide-oxidizing, or chemoautotrophic microorganisms to elongate C1 molecules to longer carbon chain organic chemicals within the bioreactor of the present invention. Finally the present invention, in certain embodiments, provides compositions and methods for the production and processing and delivery of chemical nutrients, and particularly gaseous electron donors or gaseous electron acceptors or gaseous carbon sources, or other gaseous nutrients needed for chemoautotrophic carbon-fixation by the oxyhydrogen, or hydrogen-oxidizing, or carbon monoxide-oxidizing, or chemoautotrophic microorganisms, and particularly electron donors including but not limited to molecular hydrogen, and electron acceptors including but not limited to oxygen and carbon dioxide to drive the carbon fixation reaction; compositions and methods for the maintenance of an environment conducive for carbon-fixation by oxyhydrogen or hydrogen-oxidizing, or carbon monoxide-oxidizing, or chemoautotrophic microorganisms; and compositions and methods for the removal of the chemical products of chemosynthesis and/or chemical products from biosynthetic reactions that elongate C1 molecules to longer carbon chain organic chemicals from the oxyhydrogen culture environment within the bioreactor of the present invention and the recovery and recycling of unused of chemical nutrients.

The terms "oxyhydrogen microorganism" and "knallgas microorganism" are used interchangeably throughout to refer to a microorganism that is capable of performing the oxyhydrogen reaction or more specifically a microorganism that has the ability to:

Use molecular hydrogen by means of hydrogenases with some of the electrons donated from $H_2$ being utilized for the reduction of $NAD^+$ (and/or other intracellular reducing equivalents) and the rest of the electrons for aerobic respiration Fix $CO_2$ autotrophically, through pathways such as the reverse Calvin Cycle or the reverse citric acid cycle ["Thermophilic bacteria", Jakob Kristjansson, Chapter 5, Section III, CRC Press, (1992)]

In addition, the terms "oxyhydrogen reaction" and "knallgas reaction" are used interchangeably throughout to refer to the microbial oxidation of molecular hydrogen by molecular oxygen. The oxyhydrogen reaction is generally expressed as:

$$2H_2 + O_2 \rightarrow 2H_2O + \text{energy}$$

and/or by stoichiometric equivalents of this reaction.

Exemplary oxyhydrogen microorganisms that can be used in one or more process steps of certain embodiments of the present invention and that can be grown, maintained, and cultivated in the bioreactor of the present invention include but are not limited to one or more of the following: *Rhodococcus opacus* and other *Rhodococcus* sp.; *Rhizobium japonicum* and other *Rhizobium* sp.; *Thiocapsa roseopersicina* and other *Thiocapsa* sp.; *Pseudomonas hydrogenovora*, *Pseudomonas hydrogenothermophila*, and other *Pseudomonas* sp.; *Hydrogenomonas pantotropha*, *Hydrogenomonas eutropha*, *Hydrogenomonas facilis*, and other *Hydrogenomonas* sp.; *Hydrogenobacter thermophilus* and other *Hydrogenobacter* sp.; *Hydrogenovibrio marinus* and other *Hydrogenovibrio* sp.; *Helicobacter pylori* and other *Helicobacter* sp.; *Xanthobacter* sp.; *Hydrogenophaga* sp.; *Bradyrhizobium japonicum* and other *Bradyrhizobium* sp.; *Ralstonia eutropha* and other *Ralstonia* sp.; *Alcaligenes eutrophus* and other *Alcaligenes* sp.; *Variovorax paradoxus*, and other *Variovorax* sp.; *Acidovorax facilis*, and other *Acidovorax* sp.; cyanobacteria including but not limited to *Anabaena oscillarioides*, *Anabaena spiroides*, *Anabaena cylindrica*, and other *Anabaena* sp.; green algae including but not limited to *Scenedesmus obliquus* and other *Scenedesmus* sp., *Chlamydomonas reinhardii* and other *Chlamydomonas* sp., *Ankistrodesmus* sp., *Rhaphidium polymorphium* and other *Rhaphidium* sp.; purple non-sulfur photosynthetic bacteria including but not limited to *Rhodopseudomonas palustris*, *Rhodopseudomonas capsulata*, *Rhodopseudomonas viridis*, *Rhodopseudomonas sulfoviridis*, *Rhodopseudomonas blastica*, *Rhodopseudomonas spheroides*, *Rhodopseudomonas acidophila* and other *Rhodopseudomonas* sp., *Rhodospirillum rubrum*, and other *Rhodospirillum* sp.; as well as a consortiums of microorganisms that include oxyhydrogen microorganisms.

The different oxyhydrogen microorganisms that can be used in certain embodiments of the present invention may be native to a range environments including but not limited to hydrothermal vents, geothermal vents, hot springs, cold seeps, underground aquifers, salt lakes, saline formations, mines, acid mine drainage, mine tailings, oil wells, refinery wastewater, oil, gas, or hydrocarbon contaminated waters or soils; coal seams, the deep sub-surface, waste water and sewage treatment plants, geothermal power plants, sulfatara fields, soils including but not limited to soils contaminated with hydrocarbons and/or located under or around oil or gas wells, oil refineries, oil pipelines, gasoline service stations. They may or may not be extremophiles including but not limited to thermophiles, hyperthermophiles, acidophiles, halophiles, and psychrophiles.

In some embodiments of the present invention a hydrogen-oxidizing or carbon-monoxide oxidizing microorganism having greater tolerance for oxygen than a strictly anaerobic acetogenic, or methanogenic, hydrogen-oxidizing or carbon-monoxide oxidizing microorganism is utilized in a chemosynthetic reaction step or steps occurring within the bioreactor of the present invention. In some embodiments that hydrogen-oxidizing or carbon-monoxide oxidizing microorganism is an oxyhydrogen microorganism. In some embodiments the microorganism is a cell of the class Actinobacteria. In some embodiments, the microorganism is strain of the suborder corynebacterineae (corynebacterium, gordoniaceae, mycobacteriaceae and nocardiaceae). In some embodiments the microorganisms is a cell of the family of Nocardiaceae. In some embodiments the microorganism or microorganisms are drawn from one or more of the following classifications: *Corynebacterium*, *Gordonia*, *Rhodococcus*, *Mycobacterium* and *Tsukamurella*. In some embodiments, the microorganism is a cell of the genus *Rhodococcus*. In some embodiments the cell is a strain of the species *Rhodococcus* sp., *Rhodococcus opacus*, *Rhodococcus aurantiacus*; *Rhodococcus baikonurensis*; *Rhodococcus boritolerans*; *Rhodococcus equi*; *Rhodococcus coprophilus*; *Rhodococcus corynebacterioides*; *Nocardia corynebacterioides* (synonym: *Nocardia corynebacterioides*); *Rhodococcus erythropolis*; *Rhodococcus fascians*; *Rhodococcus globerulus*; *Rhodococcus gordoniae*; *Rhodococcus jostii Rhodococcus koreensis*; *Rhodococcus kroppenstedtii*; *Rhodococcus maanshanensis*; *Rhodococcus marinonascens*; *Rhodococcus opacus*; *Rhodococcus percolatus*; *Rhodococcus phenolicus*; *Rhodococcus polyvorum*; *Rhodococcus pyridinivorans*; *Rhodococcus rhodochrous*; *Rhodococcus rhodnii*; (synonym: *Nocardia rhodnii*); *Rhodococcus ruber* (synonym: *Streptothrix rubra*); *Rhodococcus* sp. RHA1; *Rhodococcus triatomae*; *Rhodococcus tukisamuensis*; *Rhodococcus wratislaviensis* (synonym: *Tsukamurella wratislaviensis*); *Rhodococcus yunnanensis*; *Rhodococcus zopfii*. In some embodiments, the microorganism is strain *Rhodococcus opacus* DSM number 43205 or 43206. In some embodiments, the microorganism is strain *Rhodococcus* sp. DSM number 3346. In some embodiments, the microorganism is a strain within the family burkholderiaceae. In some embodiments the microorganisms is a strain within the genus *Cupriavidus* or *Ralstonia*. In some embodiments the microorganism is a strain of the species *Cupriavidus necator*. In some embodiments the microorganism is the strain *Cupriavidus necator* DSM number 531 or 541.

In some embodiments of the present invention an acetogenic microorganism is the hydrogen-oxidizing or carbon monoxide-oxidizing microorganism that is grown or maintained or cultivated in the bioreactor of the present invention. In some embodiments of the present invention a methanogenic microorganism is the hydrogen-oxidizing or carbon monoxide-oxidizing microorganism that is grown or maintained or cultivated in the bioreactor of the present invention.

In some embodiments of the present invention a methanotrophic microorganism or a microorganism that can directly consume methane as a carbon and energy source for biosynthesis is grown or maintained or cultivated in the bioreactor of the present invention.

In some embodiments, relatively long-chain chemical products can be biosynthesized within the bioreactor of the present invention. For example, the organic chemical product produced in some embodiments can include compounds with carbon chain lengths of at least C5, at least C10, at least C15, at least C20, between about C5 and about C30, between about C10 and about C30, between about C15 and about C30, or between about C20 and about C30.

In certain embodiments, organic compounds containing only one carbon atom (i.e. C1 compounds), such as carbon monoxide or carbon dioxide, are generated through the gasification and/or pyrolysis and/or partial oxidation and/or steam reforming of biomass and/or other organic matter (e.g., biomass and/or other organic matter from waste or low value sources), and provided as a syngas or producer gas to the culture of oxyhydrogen, or hydrogen-oxidizing, or carbon monoxide-oxidizing, or chemoautotrophic microorganisms contained in the bioreactor, where the ratio of hydrogen to carbon monoxide in the syngas may or may not be adjusted through means such as the water gas shift reaction, prior to the syngas or producer gas being delivered to the microbial culture in the bioreactor. In certain embodiments, organic compounds containing only one carbon atom are generated through methane steam reforming from methane or natural gas (e.g., stranded natural gas, or natural gas that would be otherwise flared or released to the atmosphere), or biogas, or landfill gas, and provided as a syngas or producer gas to the culture of oxyhydrogen or hydrogen-oxidizing, or carbon monoxide-oxidizing, or chemoautotrophic microorganisms in the bioreactor, where the ratio of hydrogen to carbon monoxide in the syngas may or may not be adjusted through means such as the water gas shift reaction, prior to the syngas being delivered to the microbial culture.

In certain embodiment of the present invention hydrogen electron donors and/or C1 carbon sources for microbial growth and biosynthesis are generated from waste or low value sources of carbon and energy using methods known in to art of chemical and process engineering including but not limited to gasification, pyrolysis, partial oxidation, or steam-reforming of feedstock such as but not limited to municipal waste, black liquor, bagasse, agricultural waste, crop residues, wood waste, saw dust, forestry residue, food waste, stranded natural gas, biogas, landfill gas, sour gas, methane hydrates, tires, pet coke, waste carpet, sewage, manure, straw, and low value, highly lignocellulosic biomass in general.

Process heat can be generated as a co-product in the production of syngas or producer gas or hydrogen. In certain embodiments of the present invention, process heat generated in syngas or producer gas or hydrogen production is recovered and utilized elsewhere in the conversion process of certain embodiments of the present invention in order to improve overall energy efficiency. A chemical and/or heat and/or electrical co-product can accompany the generation of syngas or producer gas or molecular hydrogen for use as an electron donor in certain embodiments of the present invention. The chemical and/or heat and/or electrical co-products of syngas or producer gas or molecular hydrogen generation can be used to the extent possible elsewhere in the conversion process of certain embodiments of the present invention, for example, in order to improve efficiency. In certain embodiments, excess heat or electrical energy co-product in the production of syngas or producer gas or molecular hydrogen (e.g., beyond what can be used internally in the process) can be delivered for sale, for example, for use in another chemical and/or biological process through means known in the art and science heat exchange and transfer and electrical generation and transmission, including but not limited to the conversion of process heat to electrical power in a form that can be sold for use in the electrical grid.

The electron donors and/or carbon sources that is input into the bioreactor for microbial growth and biosynthesis in certain embodiments of the present invention may also be provided by, derived, or refined from pollutants or waste products including but not limited to one or more of the following: process gas; tail gas; enhanced oil recovery vent gas; biogas; acid mine drainage; landfill leachate; landfill gas; geothermal gas; geothermal sludge or brine; metal contaminants; gangue; tailings; sulfides; disulfides; mercaptans including but not limited to methyl and dimethyl mercaptan, ethyl mercaptan; carbonyl sulfide; carbon disulfide; alkanesulfonates; dialkyl sulfides; thiosulfate; thiofurans; thiocyanates; isothiocyanates; thioureas; thiols; thiophenols; thioethers; thiophene; dibenzothiophene; tetrathionate; dithionite; thionate; dialkyl disulfides; sulfones; sulfoxides; sulfolanes; sulfonic acid; dimethylsulfoniopropionate; sulfonic esters; hydrogen sulfide; sulfate esters; organic sulfur; sulfur dioxide and all other sour gases.

Figure 8:
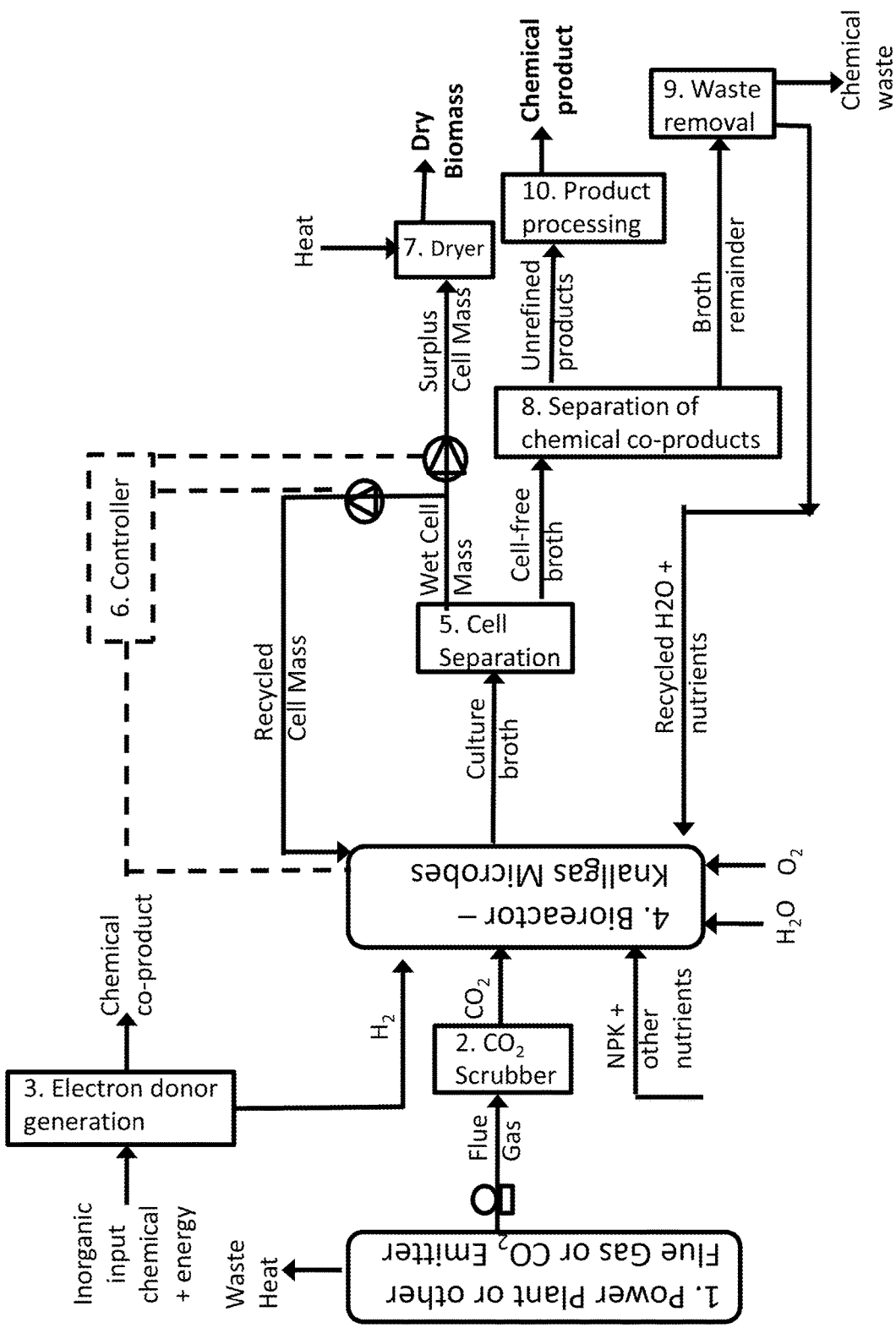
FIG. 8 is a general process flow diagram for one embodiment of this invention utilizing the bioreactor of the present invention for a carbon capture and fixation process.

FIG. 8 illustrates the general process flow diagram for embodiments of the present invention that have a process step for the generation of electron donors (e.g., molecular hydrogen electron donors) suitable for supporting chemosynthesis from an energy input and raw inorganic chemical input; followed by recovery of chemical co-products from the electron donor generation step; delivery of generated electron donors along with oxygen electron acceptors, water, nutrients, and $CO_2$ from a point industrial flue gas source, into chemosynthetic reaction step or steps occurring within the bioreactor of the present invention that make use of oxyhydrogen microorganisms to capture and fix carbon dioxide, creating chemical and biomass co-products through chemosynthetic reactions; followed by process steps for the recovery of both chemical and biomass products from the process stream; and recycling of unused nutrients and process water, as well as cell mass needed to maintain the microbial culture, back into the bioreactors where the carbon-fixation reaction steps occur.

In the embodiment illustrated in FIG. 8, the $CO_2$ containing flue gas is captured from a point source or emitter. Electron donors (e.g. $H_2$) needed for chemosynthesis can be generated from input inorganic chemicals and energy. The flue gas can be pumped through the bioreactors of the present invention containing oxyhydrogen microorganisms along with electron donors and acceptors needed to drive chemosynthesis and a medium suitable to support the microbial culture and carbon fixation through chemosynthesis. The cell culture may be continuously flowed into and out of the bioreactors. After the cell culture leaves the bioreactors, the cell mass can be separated from the liquid medium. Cell mass needed to replenish the cell culture population at a desirable (e.g., optimal) level can be recycled back into the bioreactor. Surplus cell mass can be dried to form a dry biomass product which can be further post-processed into various chemical, fuel, or nutritional products. Following the cell separation step, extracellular chemical products of the chemosynthetic reaction can be removed from the process flow and recovered. Then, any undesirable waste products that might be present are removed. Following this, the liquid medium and any unused nutrients can be recycled back into the bioreactors.

Many of the reduced inorganic chemicals upon which chemoautotrophs grow (e.g. $H_2$, $H_2S$, ferrous iron, ammonium, $Mn^{2+}$) can be readily produced using electrochemical and/or thermochemical processes known in the art of chemical engineering that may optionally be powered by a variety carbon dioxide emission-free or low-carbon emission and/or renewable sources of power including wind, hydroelectric, nuclear, photovoltaics, or solar thermal.

Certain embodiments of the present invention use carbon dioxide emission-free or low-carbon emission and/or renewable sources of power including but not limited to one or more of the following: photovoltaics, solar thermal, wind power, hydroelectric, nuclear, geothermal, enhanced geothermal, ocean thermal, ocean wave power, tidal power; for the production of electron donors, and particularly hydrogen gas. In certain embodiments of the present invention the hydrogen gas is generated from non-potable water or sea water or other sources of salt water or brine using the aforementioned low-carbon emission and/or renewable sources of power along with established electrolysis technologies. In certain embodiments of the present invention oxyhydrogen microorganisms function as biocatalysts within the bioreactor of the present invention for the conversion of renewable energy and/or low or zero carbon emission energy into liquid hydrocarbon fuel, or high energy density oleochemicals or organic compounds generally, with $CO_2$ captured from flue gases, or from the atmosphere, or ocean serving as a carbon source. These embodiments of the present invention can provide renewable energy technologies with the capability of producing a hydrocarbon transportation fuel having significantly higher energy density than if the renewable energy sources are used to produce hydrogen gas—which must be stored in relatively heavy storage systems (e.g. tanks or storage materials)—or if it is used to charge batteries, which have relatively low energy density. Additionally the liquid hydrocarbon fuel product of certain embodiments of the present invention may be more compatible with the current transportation infrastructure compared to battery or hydrogen energy storage options.

The position of the process step or steps for the generation of electron donors (e.g., molecular hydrogen electron donors) in the general process flow of certain embodiments of the present invention is illustrated in FIG. 8 by Box 3, labeled "Electron Donor Generation." Electron donors produced in certain embodiments of the present invention using electrochemical and/or thermochemical processes known in the art of chemical engineering and/or generated from natural sources include, but are not limited to molecular hydrogen and/or valence or conduction electrons in solid state electrode materials and/or other reducing agents including but not limited to one or more of the following: ammonia; ammonium; carbon monoxide; dithionite; elemental sulfur; hydrocarbons; metabisulfites; nitric oxide; nitrites; sulfates such as thiosulfates including but not limited to sodium thiosulfate ($Na_2S_2O_3$) or calcium thiosulfate ($CaS_2O_3$); sulfides such as hydrogen sulfide; sulfites; thionate; thionite; transition metals or their sulfides, oxides, chalcogenides, halides, hydroxides, oxyhydroxides, sulfates, or carbonates, in soluble or solid phases.

Certain embodiments of the present invention use molecular hydrogen as the electron donor. Hydrogen electron donors are generated by methods known in to art of chemical and process engineering including but not limited to one or more of the following: through electrolysis of water by approaches including but not limited to using Proton Exchange Membranes (PEM), liquid electrolytes such as KOH, high-pressure electrolysis, high temperature electrolysis of steam (HTES); thermochemical splitting of water through methods including but not limited to the iron oxide cycle, cerium(IV) oxide-cerium(III) oxide cycle, zinc zinc-oxide cycle, sulfur-iodine cycle, copper-chlorine cycle, calcium-bromine-iron cycle, hybrid sulfur cycle; electrolysis of hydrogen sulfide; thermochemical splitting of hydrogen sulfide; other electrochemical or thermochemical processes known to produce hydrogen with low- or no-carbon dioxide emissions including but not limited to: carbon capture and sequestration enabled methane reforming; carbon capture and sequestration enabled coal gasification; the Kvarner-process and other processes generating a carbon-black product; carbon capture and sequestration enabled gasification or pyrolysis of biomass; and the half-cell reduction of $H^+$ to $H_2$ accompanied by the half-cell oxidation of electron sources including but not limited to ferrous iron ($Fe^{2+}$) oxidized to ferric iron ($Fe^{3+}$) or the oxidation of sulfur compounds whereby the oxidized iron or sulfur can be recycled to back to a reduced state through additional chemical reaction with minerals including but not limited to metal sulfides, hydrogen sulfide, or hydrocarbons.

In certain embodiments of the present invention that utilize molecular hydrogen as an electron donor for the carbon-fixation reactions performed by oxyhydrogen, or hydrogen-oxidizing, or carbon monoxide-oxidizing, or chemoautotrophic microorganisms, there can be a chemical co-product formed in the generation of molecular hydrogen using a renewable and/or $CO_2$ emission-free energy input. If water is used as a hydrogen source, then oxygen can be a co-product of water splitting through processes including but not limited to electrolysis or thermochemical water splitting. In certain embodiments of the present invention using water as a hydrogen source, some of the oxygen co-product can be used in the oxyhydrogen carbon fixation step for the production of intracellular ATP through the oxyhydrogen reaction enzymatically linked to oxidative phosphorylation. In certain embodiments of the present invention, the oxygen produced by water-splitting in excess of what is required to maintain favorable (e.g., optimal) conditions for carbon fixation and organic compound production within the bioreactor by the oxyhydrogen microorganisms can be processed into a form suitable for sale through process steps known in the art and science of commercial oxygen gas production.

In certain embodiments, the generated electron donors are oxidized in the chemosynthetic reaction step or steps occurring within the bioreactor by electron acceptors that include but are not limited to carbon dioxide, oxygen and/or one or more of the following: ferric iron or other transition metal ions, nitrates, nitrites, sulfates, or valence or conduction band holes in solid state electrode materials.

The position of the bioreactor containing chemosynthetic and/or oxyhydrogen reaction step or steps in the general process flow of certain embodiments of the present invention is illustrated in FIG. 8 by Box 4 labeled "Bioreactor—Knallgas Microbes."

At each step in the process where chemosynthetic and/or oxyhydrogen reactions occur one or more types of electron donor and one or more types of electron acceptor may be pumped or otherwise added to the bioreactor of the present invention as either a bolus addition, or periodically, or continuously to the nutrient medium containing oxyhydrogen, or hydrogen-oxidizing, or carbon monoxide-oxidizing, or chemoautotrophic microorganisms. The chemosynthetic reaction driven by the transfer of electrons from electron donor to electron acceptor can fix inorganic carbon dioxide into organic compounds and biomass.

The culture broth used in the chemosynthetic steps of certain embodiments of the present invention may be an aqueous solution contained within the bioreactor having suitable minerals, salts, vitamins, cofactors, buffers, and other components needed for microbial growth, known to those skilled in the art [Bailey and Ollis, Biochemical Engineering Fundamentals, 2nd ed; pp 383-384 and 620-622; McGraw-Hill: New York (1986)]. These nutrients can be chosen to maximize carbon-fixation and promote the carbon flow through enzymatic pathways leading to desired organic compounds. In certain embodiments of the present invention the nutrients dissolved in aqueous solution comprise only inorganic constituents and do not include any fixed carbon nutrients such as vitamins. Alternative growth environments such as those used in the arts of solid state or non-aqueous fermentation may be used in certain embodiments. In certain embodiments that utilize an aqueous culture, broth, salt water, sea water, or other non-potable sources of water may be used within the bioreactor when tolerated by the microorganisms.

The biochemical pathways expressed within the bioreactor environment may be controlled and optimized in certain embodiments of the present invention for the production of chemical products (e.g., targeted organic compounds) and/or biomass by maintaining specific growth conditions (e.g., levels of nitrogen, oxygen, phosphorous, sulfur, trace micronutrients such as inorganic ions, and if present any regulatory molecules that might not generally be considered a nutrient or energy source). Depending upon the embodiment of the invention the broth and bioreactor may be maintained in aerobic, microaerobic, anoxic, or anaerobic conditions. The oxygen level is controlled in certain embodiments of the invention. The oxygen level can be controlled, for example, to enhance the production of targeted organic compounds by the oxyhydrogen microorganisms through carbon-fixation. One objective of controlling oxygen levels, in certain embodiments, is to control (e.g., optimize) the intracellular Adenosine Triphosphate (ATP) concentration through the cellular reduction of oxygen and production of ATP by oxidative phosphorylation. In some such embodiments, it can be desirable, while controlling ATP concentration, to simultaneously keep the environment sufficiently reducing so that the intracellular ratio of NADH (or NADPH) to NAD (or NADP) remains relatively high. The maintenance of high intracellular concentrations of ATP as well as NADH and/or NADPH within the bioreactor is targeted in certain embodiments of the present invention to promote carbon fixation and drive anabolic pathways and/or solventogenic pathways that consume reducing equivalents and either consume ATP, and/or that lower the net ATP yield of chemosynthetic carbon-fixation. Such biochemical pathways include but are not limited to the following: fatty acid synthesis; amino acid synthesis; mevalonate pathway and terpenoid synthesis; butanol pathway and 1-butanol synthesis; acetolactate/alpha-ketovalerate pathway and 2-butanol synthesis; and the ethanol pathway. A preferred oxygen level within the bioreactor can be determined, in some embodiments of in the present invention: too low an oxygen level can reduce the intracellular ATP in oxyhydrogen microorganisms below a desired level, while too high an oxygen level can decrease the NADH (or NADPH) to NAD (or NADP) ratio below a desired level.

In certain embodiments of the present invention short chain organic acids, from C1 to C4 in length, are not a product of cellular respiration in the bioreactor.

In certain embodiments of the present invention methane is not a product of cellular respiration in the bioreactor.

In some embodiments of the present invention the fatty acid biosynthesis is expressed by microorganisms within the bioreactor. Fatty acid biosynthesis involves net ATP consumption. For example the following gives the net reaction for synthesis of Palmitic acid (C16), in this example starting from Acetyl-CoA:

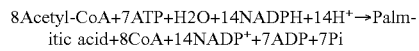
8Acetyl-CoA+7ATP+H2O+14NADPH+14H$^+$→Palmitic acid+8CoA+14NADP$^+$+7ADP+7Pi In some embodiments of the present invention the microorganism in the bioreactor is able to produce more than one ATP per 4 H2 molecules oxidized for cellular respiration. In some embodiments of the present invention the microorganism in the bioreactor is able to produce two ATP per $H_2$ molecule oxidized for cellular respiration. In some embodiments of the present invention the microorganism in the bioreactor is able to produce between two and three ATP per $H_2$ molecule oxidized for cellular respiration. In some embodiments of the present invention the microorganism in the bioreactor is able to produce more eight times more ATP per $H_2$ consumed than methanogenic or acetogenic microorganisms. In some embodiments of the present invention this microorganism is an oxyhydrogen or knallgas microbe.

In some embodiments of the present invention the microorganism in the bioreactor generates water as a product of oxidizing $H_2$ for cellular respiration. In some embodiments this microorganism is an oxyhydrogen or knallgas microbe.

In some embodiments of the present invention utilizing oxyhydrogen or knallgas microbes, the water product of cellular respiration is used to reduce water inputs into the bioprocess and the bioreactor. In some embodiments of the present invention the products of cellular respiration from the microorganisms in the bioreactor are non-toxic to the microorganism and do not inhibit growth or biosynthesis by the microorganism. In some embodiments of the present invention the products of cellular respiration from the microorganisms in the bioreactor are not acidic.

In some embodiments of the present invention an oil or oleochemical is produced with an energy density greater than 36.1 MJ/kg.

Biomass lipid content and lipid biosynthetic pathway efficiency are two factors that can affect the overall efficiency of certain embodiments of the present invention for converting CO, $CO_2$ and other C1 compounds to longer chain lipid compounds. The biomass lipid content can determine the proportion of carbon and reducing equivalents directed towards the synthesis of lipid, bio-based oil, or oleochemical products, as opposed to other components of biomass. The lipid content can determine the amount of energy input from the reducing equivalents that can be captured in final fuel product. Likewise, the metabolic pathway efficiency can determine the amount of reducing equivalents that must be consumed in converting CO and/or $CO_2$ and hydrogen to lipid along the lipid biosynthetic pathway. Many oxyhydrogen microorganisms include species rich in lipid content and containing efficient pathways from $H_2$ and $CO_2$ to lipid. Certain embodiments of the present invention use oxyhydrogen species with high lipid contents such as but not limited to *Rhodococcus opacus* which can have a lipid content of over 70% [Gouda, M. K., Omar, S. H., Chekroud, Z. A. & Nour Eldin, H. M. Biore-mediation of kerosene I: A case study in liquid media. Chemosphere 69, 1807-1814, doi:S0045-6535(07)00738-2; Waltermann, M., Luftmann, H., Baumeister, D., Kalscheuer, R. & Steinbuchel, A. *Rhodococcus opacus* strain PD630 as a new source of high-value single-cell oil? Isolation and characterization of triacylglycerols and other storage lipids. Microbiology 146 (Pt 5), 1143-1149 (2000).]. Certain embodiments of the present invention use oxyhydrogen species utilizing highly efficiency metabolic pathways such as but not limited to the reverse tricarboxylic acid cycle [i.e. reverse citric acid cycle] to fix carbon [Miura, A., Kameya, M., Arai, H., Ishii, M. & Igarashi, Y. A soluble NADH-dependent fumarate reductase in the reductive tricarboxylic acid cycle of *Hydrogenobacter thermophilus* TK-6. J Bacteriol 190, 7170-7177, doi:JB.00747-08 [pii] 10.1128/JB.00747-08 (2008); Shively, J. M., van Keulen, G. & Meijer, W. G. Something from almost nothing: carbon dioxide fixation in chemoautotrophs. Annu Rev Microbiol 52, 191-230, doi:10.1146/annurev.micro.52.1.191 (1998).].

The source of inorganic carbon used in the chemosynthetic reaction process steps contained within the bioreactor of certain embodiments of the present invention includes but is not limited to one or more of the following: a carbon dioxide-containing gas stream that may be pure or a mixture; liquefied $CO_2$; dry ice; dissolved carbon dioxide, carbonate ion, or bicarbonate ion in solutions including aqueous solutions such as sea water; inorganic carbon in a solid form such as a carbonate or bicarbonate minerals. Carbon dioxide and/or other forms of inorganic carbon can be introduced to the nutrient medium contained in the bioreactor either as a bolus addition, periodically, or continuously at the steps in the process where carbon-fixation occurs. Organic compounds containing only one carbon atom, which can be used in the biosynthetic reaction process steps occurring in the bioreactor of certain embodiments of the present invention include but are not limited to one or more of the following: carbon monoxide, methane, methanol, formate, formic acid, and/or mixtures containing C1 chemicals including but not limited to various syngas or producer compositions generated from various gasified, pyrolyzed, partially oxidized, or steam-reformed fixed carbon feedstocks or C1 containing industrial or mining or drilling tail gases, process gases, or effluent streams.

In certain embodiments of the present invention, carbon dioxide containing flue gases are captured from the smoke stack at temperature, pressure, and gas composition characteristic of the untreated exhaust, and directed with minimal modification into the bioreactor of the present invention containing a chemoautotrophic microorganism where carbon-fixation occurs. In some embodiments in which impurities harmful to chemoautotrophic organisms are not present in the flue gas, modification of the flue gas upon entering the bioreactor can be limited to the compression needed to pump the gas through the bioreactor system and/or the heat exchange needed to lower the gas temperature to one suitable for the microorganisms.

The $O_2$ content of a typical industrial or power plant flue gas is 2-6%. In certain embodiments of the present invention carbon capture from a flue gas stream is performed by a hydrogen-oxidizing microorganism contained in the bioreactor that is tolerant of gas input and bioreactor headspace oxygen levels ranging from 2-6%. In some embodiments this hydrogen-oxidizing microorganism is an oxyhydrogen microorganism.

Gases in addition to carbon dioxide that are dissolved into solution and fed to the culture broth or dissolved directly into the culture broth contained in the bioreactor in certain embodiments of the present invention include gaseous electron donors (e.g., hydrogen gas or carbon monoxide gas), but in certain embodiments of the present invention, may include other electron donors such as but not limited to other gas constituents of syngas, hydrogen sulfide, and/or other sour gases.

A controlled amount of oxygen can be maintained in the culture broth in the bioreactor for some embodiments of the present invention, and in certain embodiments, oxygen will be actively dissolved into solution fed to the culture broth in bioreactor and/or directly dissolved into the culture broth in the bioreactor.

The dissolution of oxygen, carbon dioxide and/or electron donor gases such as but not limited to hydrogen and/or carbon monoxide, into solution within the bioreactor can be achieved in some embodiments of the present invention using a system of compressors, flowmeters, and/or flow valves known to one skilled in the art of bioreactor scale microbial culturing, which can be fed into the eductor or venturi equipment in bioreactor of the present invention.

In certain embodiments of the present invention utilizing hydrogen as electron donor, the headspace gas composition is controlled such that the range of explosive hydrogen concentrations in air is 4 to 74.5% is avoided.

Additional chemicals required or useful for the maintenance and growth of oxyhydrogen, or hydrogen-oxidizing, or carbon monoxide-oxidizing, or chemoautotrophic, or heterotrophic microorganisms as known in the art can be added to the culture broth in the bioreactor of certain embodiments of the present invention. These chemicals may include but are not limited to: nitrogen sources such as ammonia, ammonium (e.g. ammonium chloride ($NH_4Cl$), ammonium sulfate (($NH_4$)$_2SO_4$)), nitrate (e.g. potassium nitrate ($KNO_3$)), urea or an organic nitrogen source; phosphate (e.g. disodium phosphate ($Na_2HPO_4$), potassium phosphate ($KH_2PO_4$), phosphoric acid ($H_3PO_4$), potassium dithiophosphate ($K_3PS_2O_2$), potassium orthophosphate ($K_3PO_4$), dipotassium phosphate ($K_2HPO_4$)); sulfate; yeast extract; chelated iron; potassium (e.g. potassium phosphate ($KH_2PO_4$), potassium nitrate ($KNO_3$), potassium iodide (KI), potassium bromide (KBr)); and other inorganic salts, minerals, and trace nutrients (e.g. sodium chloride (NaCl), magnesium sulfate ($MgSO_4$ $7H_2O$) or magnesium chloride ($MgCl_2$), calcium chloride ($CaCl_2$) or calcium carbonate ($CaCO_3$), manganese sulfate ($MnSO_4$ $7H_2O$) or manganese chloride ($MnCl_2$), ferric chloride ($FeCl_3$), ferrous sulfate ($FeSO_4$ $7H_2O$) or ferrous chloride ($FeCl_2$ $4H_2O$), sodium bicarbonate ($NaHCO_3$) or sodium carbonate ($Na_2CO_3$), zinc sulfate ($ZnSO_4$) or zinc chloride ($ZnCl_2$), ammonium molybdate ($NH_4MoO_4$) or sodium molybdate ($Na_2MoO_4$ $2H_2O$), cuprous sulfate ($CuSO_4$) or copper chloride ($CuCl_2$ $2H_2O$), cobalt chloride ($CoCl_2$ $6H_2O$), aluminum chloride ($AlCl_3.6H_2O$), lithium chloride (LiCl), boric acid ($H_3BO_3$), nickel chloride $NiCl_2$ $6H_2O$, tin chloride ($SnCl_2$ $H_2O$), barium chloride ($BaCl_2$ $2H_2O$), copper selenate ($CuSeO_4$ $5H_2O$) or sodium selenite ($Na_2SeO_3$), sodium metavanadate ($NaVO_3$), chromium salts). In certain embodiments the mineral salts medium (MSM) formulated by Schlegel et al may be used ["Thermophilic bacteria", Jakob Kristjansson, Chapter 5, Section III, CRC Press, (1992)].

In certain embodiments, the concentrations of nutrient chemicals (e.g., the electron donors and acceptors), are maintained at favorable levels (e.g., as close as possible to their respective optimal levels) for enhanced (e.g., maximum) carbon uptake and fixation and/or production of organic compounds, which varies depending upon the oxyhydrogen, or hydrogen-oxidizing, or carbon monoxide-oxidizing, or chemoautotrophic species utilized but is known or determinable without undue experimentation to one of ordinary skill in the art of microbiology and bioprocess engineering.

Along with nutrient levels, the waste product levels, pH, temperature, salinity, dissolved oxygen and carbon dioxide, gas and liquid flow rates, agitation rate, and pressure in the bioreactor are controlled in certain embodiments of the present invention. In certain embodiments the operating parameters affecting carbon-fixation can be monitored with sensors (e.g. using a dissolved oxygen probe and/or an oxidation-reduction probe to gauge electron donor/acceptor concentrations) and can be controlled either manually or automatically based upon feedback from sensors through the use of equipment including but not limited to actuating valves, pumps, and agitators. The temperature of the incoming broth as well as incoming gases can be regulated by means such as but not limited to heat exchangers.

The dissolution of gases and nutrients needed to maintain the microbial culture in the bioreactor, and in certain embodiments to promote carbon-fixation, as well as the removal of inhibitory waste products, can be enhanced by agitation of the culture broth. In certain embodiments of the present invention the agitation needed is generated by the system of liquid circulation pumps, down tubes, and eductors or venturis of the bioreactor in the present invention. Thus agitation of the culture broth in certain embodiments of the present invention can be accomplished by recirculation of broth from the bottom of the bioreactor through the down tube, and eductor or venturi and by the consequent sparging of the broth with gases such as but not limited to carbon dioxide, electron donor gas (e.g. producer gas, syngas, tail gas, $H_2$, or CO), oxygen and/or air.

In certain embodiments of the present invention, the chemical environment, microorganisms, electron donors, electron acceptors, oxygen, pH, and/or temperature levels are varied either spatially and/or temporally over a series of bioreactors in fluid communication, such that a number of different carbon-fixation reactions and/or biochemical pathways to organic compounds are carried out sequentially or in parallel.

The nutrient medium containing microorganisms can be removed from the bioreactors in certain embodiments of the present invention partially or completely, periodically or continuously, and can be replaced with fresh cell-free medium, for example, to maintain the cell culture in an exponential growth phase, or to maintain the cell culture in a growth phase (either exponential or stationary) exhibiting enhanced (e.g., optimal) carbon-fixation rates, or to replenish the depleted nutrients in the growth medium, or remove inhibitory waste products.

In certain embodiments, surplus biomass is produced in the bioreactor. Surplus growth of cell mass can be removed from the bioreactor to produce a biomass product. In some embodiments, surplus growth of cell mass can be removed from the bioreactor in order to maintain a desirable (e.g., an optimal) microbial population and cell density in the microbial culture. In some embodiments a desirable (e.g., an optimal) microbial population and cell density in the microbial culture is maintained for continued high carbon capture and fixation rates.

The bioreactor base, siding, walls, lining, and/or top in certain embodiments of the present invention can be constructed out of one or more materials including but not limited to bitumen, cement, ceramics, clay, concrete, epoxy, fiberglass, glass, macadam, plastics, sand, sealant, soil, steels or other metals and their alloys, stone, tar, wood, and any combination thereof. In certain embodiments of the present invention where the microorganisms either require a corrosive growth environment and/or produce corrosive chemicals through the carbon-fixation reaction, corrosion resistant materials can be used to line the interior of the bioreactor contacting the growth medium.

In certain embodiments of the present invention the bioreactor can be located and run without the diurnal, geographical, meteorological, or seasonal constraints typically associated with photosynthetically based microbial systems due to the utilization of chemoautotrophic microorganism in the bioprocess, which lack of a direct light requirement, and the relatively protective, closed, culture environment enabled by the bioreactor of the present invention, compared to the open shallow ponds or thin-walled transparent photobioreactors utilized in photosynthetically based microbial systems.

The closed, culture environment enabled by the bioreactor of the present invention greatly reduces the interfaces across which losses of water, nutrients, and/or heat can occur, and/or through which the introduction of contaminating, invasive, competing, or predatory organisms into the reactor can occur, compared to photosynthetic based technologies for carbon-fixation or biosynthesis which are generally prone to high losses of water, nutrients, and/or heat, as well as losses due to contamination or predation due to being relatively open and unprotected systems.

The lack of dependence on light for oxyhydrogen, hydrogen-oxidizing, carbon monoxide-oxidizing, or chemoautotrophic microorganisms used in certain embodiments of the present invention can allow bioreactor and plant designs with a much smaller footprint than those traditionally associated with photosynthetic approaches. For example, the bioreactor design of the present invention is well suited to minimizing plant footprint by having the geometry suitable for application in a long vertical shaft type bioreactor system. A bioreactor of the long vertical shaft type is described, for example, in U.S. Pat. Nos. 4,279,754, 5,645,726, 5,650,070, and 7,332,077.

The bioreactors of the present invention can, in some embodiments, maintain an aerobic, microaerobic, anoxic, anaerobic, or facultative environment depending upon the embodiment of the present invention. For example, similar to the design of many sewage treatment facilities, in certain embodiments of the present invention, bioreactors are arranged in a sequence, with serial forward fluid communication, where certain bioreactors are maintained in aerobic conditions and others are maintained in anaerobic conditions, in order to perform in certain embodiments multiple chemosynthetic, and in certain embodiments, heterotrophic, bioprocessing steps on the gas and liquid process stream.

Inoculation of the microbial culture into the bioreactors of the present invention can be performed by methods including but not limited to transfer of culture from an existing microbial culture inhabiting another bioreactor of certain embodiments of the present invention and/or incubation from a seed stock raised in an incubator. The seed stock of microbial strains can be transported and stored in forms including but not limited to a powder, a liquid, a frozen form, or a freeze-dried form as well as any other suitable form, which may be readily recognized by one skilled in the art. In certain embodiments in which a culture is established in a very large reactor of the present invention, growth and establishment of cultures can be performed in progressively larger intermediate scale containers prior to inoculation of the full scale vessel.

The position of the process step or steps for the separation of cell mass from the process stream in the general process flow of certain embodiments of the present invention is illustrated in FIG. 8 by Box 5, labeled "Cell Separation".

Separation of cell mass from liquid suspension can be performed by methods known in the art of microbial culturing [Examples of cell mass harvesting techniques are given in International Patent Application No. WO08/00558, published Jan. 8, 1998; U.S. Pat. Nos. 5,807,722; 5,593,886 and 5,821,111.] including but not limited to one or more of the following: centrifugation; flocculation; flotation; filtration using a membranous, hollow fiber, spiral wound, or ceramic filter system; vacuum filtration; tangential flow filtration; clarification; settling; hydrocyclone; belt pressing. In certain embodiments where the cell mass is immobilized on a matrix, it can be harvested by methods including but not limited to gravity sedimentation or filtration, and separated from the growth substrate by liquid shear forces.

In certain embodiments of the present invention, if an excess of cell mass has been removed from the bioreactor culture, it can be recycled back into the bioreactor as indicated by the process arrow labeled "Recycled Cell Mass" in FIG. 8, along with fresh broth such that sufficient biomass is retained in the bioreactor. In certain embodiments this can allow for continued enhanced (e.g., optimal) autotrophic carbon-fixation and production of organic compounds. In certain embodiments the cell mass recovered by the harvesting system can be recycled back into the bioreactor, for example, using an airlift or geyser pump. In certain embodiments, the cell mass recycled back into the culture vessel is not exposed to flocculating agents, unless those agents are non-toxic to the microorganisms.

In certain embodiments of the present invention, the microbial culture and is maintained in the bioreactor using continuous influx and removal of nutrient medium and/or biomass, in steady state where the cell population and environmental parameters (e.g. cell density, chemical concentrations) within the bioreactor are targeted at a constant (e.g., optimal) level over time. Cell densities can be monitored in the bioreactor in certain embodiments of the present invention by direct sampling, by a correlation of optical density to cell density, and/or with a particle size analyzer. The hydraulic and biomass retention times in the bioreactor can be decoupled so as to allow independent control of both the broth chemistry and the cell density. In certain embodiments dilution rates can be kept high enough so that the hydraulic retention time in the bioreactor is relatively low compared to the biomass retention time, resulting in a highly replenished broth for cell growth. In certain embodiments dilution rates can be set at an optimal trade-off between culture broth replenishment, and increased process costs from pumping, increased inputs, and other demands that rise with dilution rates.

To assist in the processing of the biomass product into bio-based oils, oleochemicals, biofuels or other useful products, depending upon the embodiment, the surplus microbial cells in certain embodiments of the invention can be broken open following the cell recycling step using, for example, methods including but not limited to ball milling, cavitation pressure, sonication, or mechanical shearing.

The harvested biomass in some embodiments can be dried in the process step or steps of Box 7, labeled "Dryer" in the general process flow of certain embodiments of the present invention illustrated in FIG. 8.

Surplus biomass drying can be performed in certain embodiments of the present invention using technologies including but not limited to centrifugation, drum drying, evaporation, freeze drying, heating, spray drying, vacuum drying, and/or vacuum filtration. In certain embodiments, process heat generated as a co-product of syngas or producer gas generation can be used in drying the biomass. Heat waste from the industrial source of tail gas or flue gas can be used in drying the biomass, in certain embodiments. In certain embodiments of the present invention waste heat can be used in drying the biomass.

In certain embodiments of the invention, the biomass is further processed following drying to complete the production of bio-based oils, oleochemicals, or biofuels or other useful chemicals through the separation of the lipid content or other targeted biochemicals from the microbial biomass. The separation of the lipids can be performed by using nonpolar solvents to extract the lipids such as, but not limited to, hexane, cyclohexane, ethyl ether, alcohol (isopropanol, ethanol, etc.), tributyl phosphate, supercritical carbon dioxide, trioctylphosphine oxide, secondary and tertiary amines, or propane. Other useful biochemicals can be extracted using solvents including but not limited to: chloroform, acetone, ethyl acetate, and tetrachloroethylene.

In certain embodiments the extracted lipid content of the biomass can be processed using methods known in the art and science of biomass refining including but not limited to one or more of the following—catalytic cracking and reforming; decarboxylation; hydrotreatment; isomerization—to produce hydrocarbon petroleum and petrochemical replacements, including but not limited to one or more of the following: JP-8 jet fuel, diesel, gasoline, and other alkanes, olefins and aromatics. In some embodiments, the extracted lipid content of the biomass can be converted to ester-based fuels, such as biodiesel (fatty acid methyl ester or fatty acid ethyl ester), through processes known in the art and science of biomass refining including but not limited to transesterification and esterification.

In some embodiments the broth left over following the removal of cell mass can be pumped to a system for removal of the chemical products of chemosynthesis and/or spent nutrients which are recycled or recovered to the extent possible and/or disposed of.

The position of the process step or steps for the recovery of chemical products from the process stream in the general process flow of certain embodiments of the present invention is illustrated in FIG. 8 by Box 8, labeled "Separation of chemical co-products."

Recovery and/or recycling of chemosynthetic chemical products and/or spent nutrients from the aqueous broth solution can be accomplished in certain embodiments of the present invention using equipment and techniques known in the art of process engineering, and targeted towards the chemical products of particular embodiments of the present invention, including but not limited to: solvent extraction; water extraction; distillation; fractional distillation; cementation; chemical precipitation; alkaline solution absorption; absorption or adsorption on activated carbon, ion-exchange resin or molecular sieve; modification of the solution pH and/or oxidation-reduction potential, evaporators, fractional crystallizers, solid/liquid separators, nanofiltration, and all combinations thereof.

In certain embodiments of the present invention, free fatty acids, lipids, or other medium or long chain organic compounds appropriate for refinement to oleochemical or biofuel products that have been produced through chemosynthesis can be recovered from the process stream at the step at Box 8 in FIG. 8. These free organic molecules can be released into the process stream solution from the oleaginous microorganisms through means including but not limited to cellular excretion or secretion or cell lysis. In certain embodiments of the present invention, the recovered organic compounds are processed using methods known in the art and science of biomass refining.

In some embodiments, following the recovery of chemical products from the process stream, the removal of the waste products is performed as indicated by Box 9, labeled "Waste removal" in FIG. 8. In some embodiments the remaining broth is returned to the bioreactor along with replacement water and/or nutrients.

In certain embodiments of the present invention a solution of oxidized metal cations can accumulate in the bioreactor broth or be present in bioreactor effluent. A solution rich in dissolved metal cations can result from a particularly dirty flue gas or tail gas input to the process in certain embodiments such as flue gas from a coal fired plant or syngas or producer gas from gasified municipal solid waste. In some such embodiments of the present invention, the process stream can be stripped of metal cations by methods including but not limited to: cementation on scrap iron, steel wool, copper or zinc dust; chemical precipitation as a sulfide or hydroxide precipitate; electrowinning to plate a specific metal; absorption on activated carbon or an ion-exchange resin, modification of the solution pH and/or oxidation-reduction potential, solvent extraction. In certain embodiments of the present invention, the recovered metals can be sold for an additional stream of revenue.

In certain embodiments, the chemicals that are used in processes for the recovery of chemical products, the recycling of nutrients and water, and the removal of waste have low toxicity for humans, and if exposed to the process stream that is recycled back into the growth container, low toxicity for the oxyhydrogen microorganisms being used.

In certain embodiments of the present invention, the pH of the microbial culture is controlled in the bioreactor. In certain embodiments neutralization of acid in the broth can be accomplished by the addition of bases including but not limited to: limestone, lime, sodium hydroxide, ammonia, caustic potash, magnesium oxide, iron oxide. In certain embodiments, the base is produced from a carbon dioxide emission-free source such as naturally occurring basic minerals including but not limited to calcium oxide, magnesium oxide, iron oxide, iron ore, olivine containing a metal oxide, serpentine containing a metal oxide, ultramafic deposits containing metal oxides, and underground basic saline aquifers. If limestone is used for neutralization, then carbon dioxide will generally be released, which in certain embodiments can be directed back into the bioreactor for uptake by chemosynthesis.

An additional feature of certain embodiments of the present invention relates to the uses of organic compounds and/or biomass produced through the chemosynthetic or heterotrophic process step or steps occurring in the bioreactor or bioreactors of certain embodiments of the present invention. Biochemicals, oleochemicals, or fuels that can be produced using the bioreactor, microorganisms, and processes of the present invention include but are not limited to JP-8 jet fuel, diesel, gasoline, octane, biodiesel, butanol, ethanol, propanol, isopropanol, propane, alkanes, olefins, aromatics, fatty alcohols, fatty acid esters, alcohols; the production of organic chemicals including but not limited to 1,3-propanediol, 1,3-butadiene, 1,4-butanediol, 3-hydroxypropionate, 7-ADCA/cephalosporin, ε-caprolactone, γ-valerolactone, acrylate, acrylic acid, adipic acid, ascorbate, aspartate, ascorbic acid, aspartic acid, caprolactam, carotenoids, citrate, citric acid, DHA, docetaxel, erythromycin, ethylene, gamma butyrolactone, glutamate, glutamic acid, HPA, hydroxybutyrate, isopentenol, isoprene, isoprenoids, itaconate, itaconic acid, lactate, lactic acid, lanosterol, levulinic acid, lycopene, lysine, malate, malonic acid, peptides, omega-3 DHA, omega fatty acids, paclitaxel, PHA, PHB, polyketides, polyols, propylene, pyrrolidones, serine, sorbitol, statins, steroids, succinate, terephthalate, terpenes, THF, rubber, wax esters, polymers, commodity chemicals, industrial chemicals, specialty chemicals, paraffin replacements, additives, nutritional supplements, neutraceuticals, pharmaceuticals, pharmaceutical intermediates, personal care products; as raw material and/or feedstock for manufacturing or chemical processes; as feed stock for alcohol or other biofuel fermentation and/or gasification and liquefaction processes and/or other biofuel production processes including but not limited to catalytic cracking, direct liquefaction, Fisher Tropsch processes, hydrogenation, methanol synthesis, pyrolysis, transesterification, or microbial syngas conversions; as a biomass fuel for combustion in particular as a fuel to be co-fired with fossil fuels; as sources of pharmaceutical, medicinal or nutritional substances; as a carbon source for large scale fermentations to produce various chemicals including but not limited to commercial enzymes, antibiotics, amino acids, vitamins, bioplastics, glycerol, or 1,3-propanediol; as a nutrient source for the growth of other microbes or organisms; as feed for animals including but not limited to cattle, sheep, chickens, pigs, or fish; as feed stock for methane or biogas production; as fertilizer; soil additives and soil stabilizers.

In certain embodiments of the present invention the microorganism in the bioreactor has been modified using methods known in the art of artificial breeding including but not limited to accelerated mutagenesis (e.g. using ultraviolet light or chemical treatments), genetic engineering or modification, hybridization, synthetic biology or traditional selective breeding. For certain embodiments of the present invention a consortium of microorganisms is utilized, the community of which can be enriched with desirable microorganisms using methods known in the art of microbiology through growth in the presence of targeted electron donors including but not limited to hydrogen or carbon monoxide, acceptors including but not limited to oxygen, and environmental conditions.

In order to give specific examples of overall biological and chemical processes utilizing the bioreactor of the present invention, a process flow diagram describing a specific embodiment of the present invention using oxyhydrogen microorganisms contained in the bioreactor of the present invention to capture $CO_2$ and produce biomass and other useful co-products is now provided and described. This specific example should not be construed as limiting the present invention in any way and is provided for the sole purpose of illustration.

Figure 9:
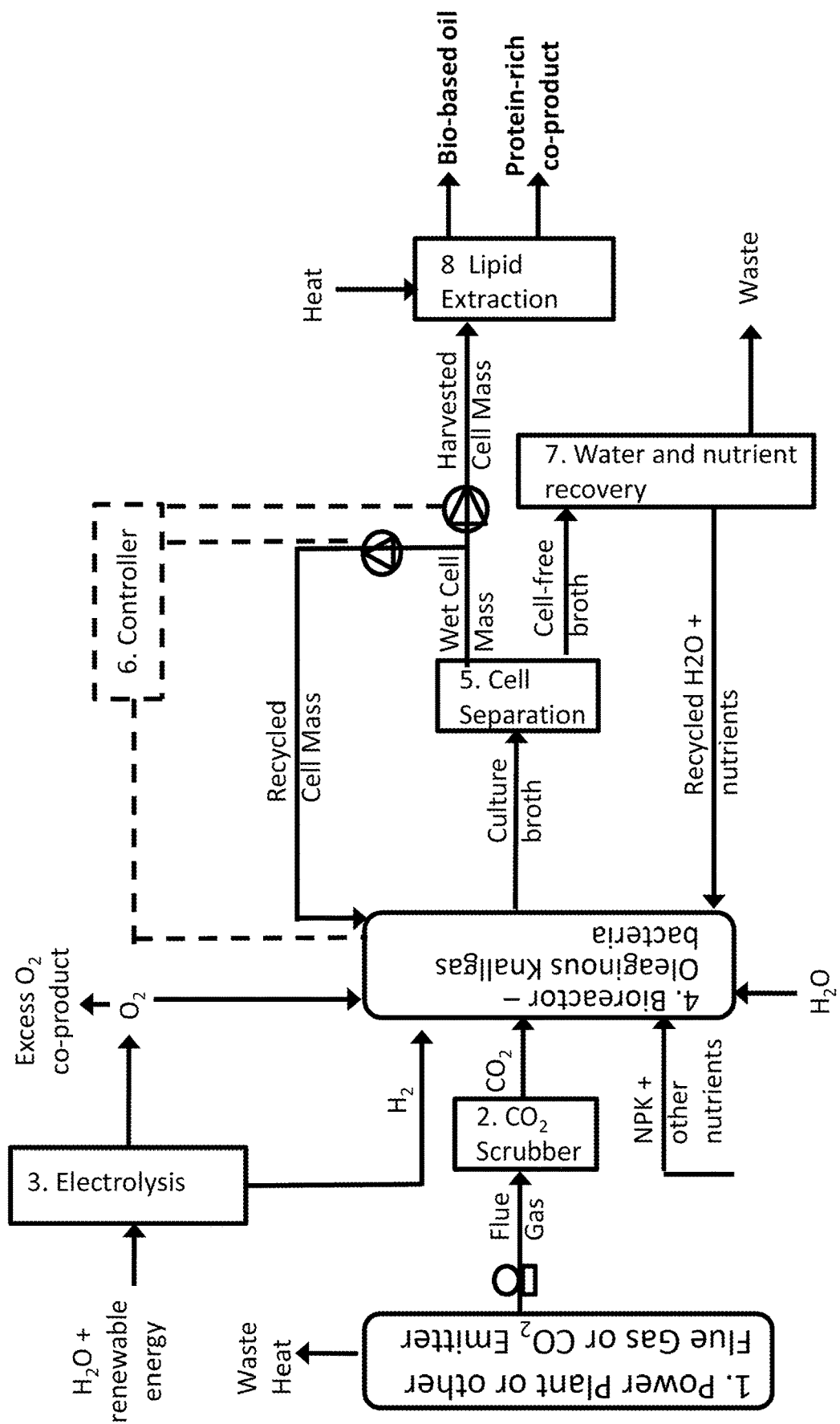
FIG. 9 is a process flow diagram for another embodiment of the present invention with conversion of syngas to lipids within the bioreactor of the present invention performed by a microorganism capable of the oxyhydrogen reaction and synthesizing lipid-rich biomass where the lipids are extracted to produce a bio-oil.
Figure 10:
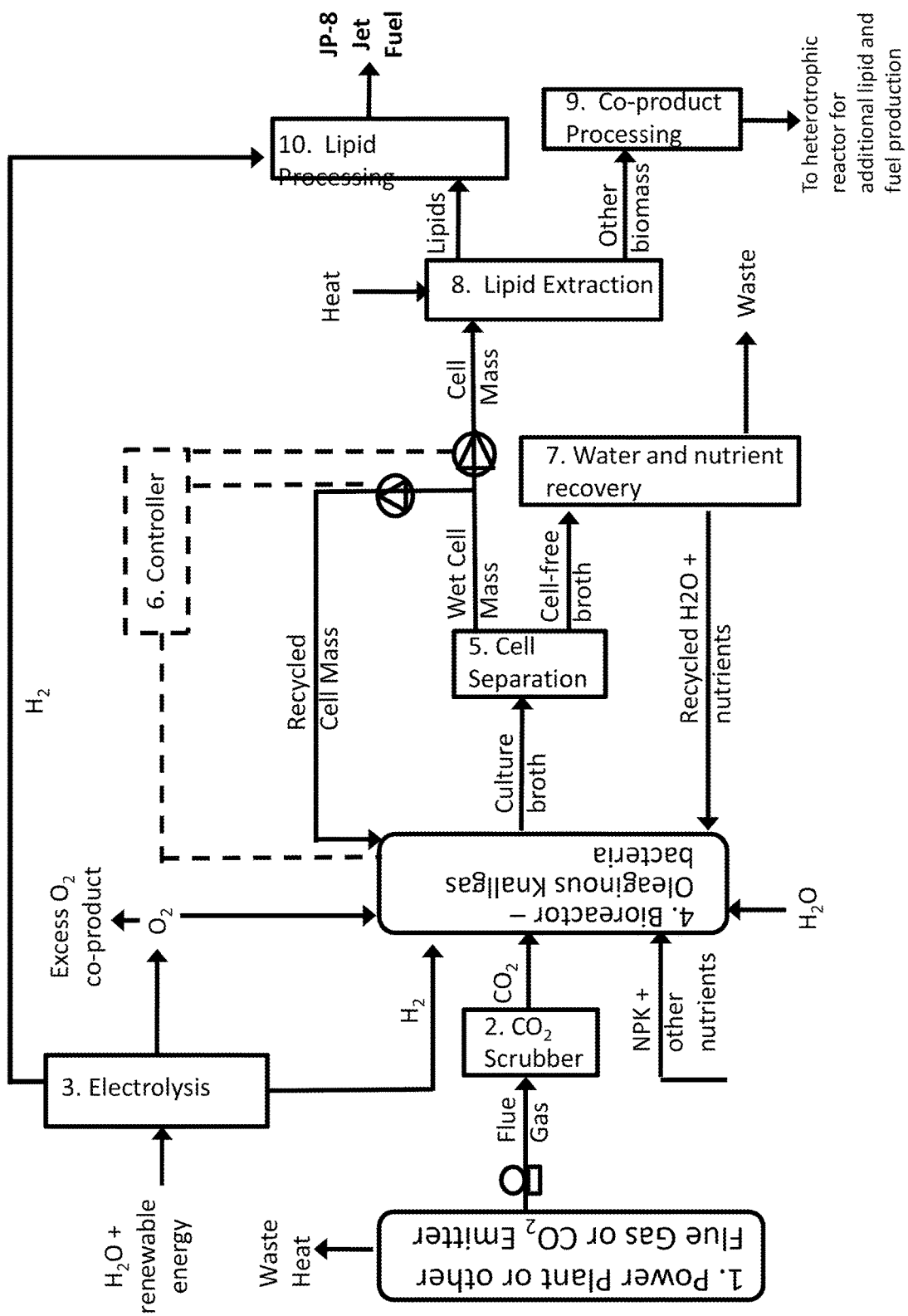
FIG. 10 is a process flow diagram for another embodiment of the present invention with capture of CO2 performed by a microorganism capable of performing an oxyhydrogen reaction (e.g., hydrogen oxidizing oleaginous microorganism such as a species in the *Rhodococcus* genus in certain embodiments) that is cultivated within the bioreactor of the present invention to produce a lipid-rich biomass that is converted into JP-8 jet fuel.

FIG. 9 includes an exemplary process flow diagram illustrating one embodiment of the present invention using a bioreactor for the capture of $CO_2$ by oxyhydrogen microorganisms and the production of lipid rich biomass from which a bio-based oil can be extracted. FIG. 10 shows a process where this bio-based oil is processed further to JP-8 jet fuel. In this set of embodiments, a carbon dioxide-rich flue gas is captured from an emission source such as a power plant, refinery, or cement producer. The flue gas can then be compressed and pumped into bioreactors containing one or more oxyhydrogen microorganisms such as but not limited to: *Rhodococcus opacus*.

In the set of embodiments illustrated in FIG. 9, hydrogen electron donor and oxygen and carbon dioxide electron acceptors are added continuously to the growth broth along with other nutrients required for chemosynthesis and culture maintenance and growth that are pumped into the bioreactor. In certain embodiments, the hydrogen source is a carbon dioxide emission-free process. Exemplary carbon dioxide emission-free processes include, for example, electrolytic or thermochemical processes powered by energy technologies including but not limited to photovoltaics, solar thermal, wind power, hydroelectric, nuclear, geothermal, enhanced geothermal, ocean thermal, ocean wave power, tidal power. In the set of embodiments illustrated in FIG. 9, oxygen serves as an electron acceptor in the chemosynthetic reaction for the intracellular production of ATP through the oxyhydrogen reaction linked to oxidative phosphorylation. The oxygen can originate from the flue gas, it can be generated from the water-splitting reaction used to produce the hydrogen, and/or it can be taken from air. In FIG. 9, carbon dioxide from the flue gas serves as an electron acceptor for the synthesis of organic compounds through biochemical pathways utilizing the ATP produced through the oxyhydrogen reaction and NADH and/or NADPH produced from the intracellular enzymatically catalyzed reduction of $NAD^+$ or $NADP^+$ by $H_2$. The culture broth can be continuously removed from the bioreactor and flowed through membrane filters to separate the cell mass from the broth. The cell mass can then be recycled back into the bioreactor and/or pumped to post-processing where lipid extraction is performed according to methods known to those skilled in the art. The lipids can then be converted to JP-8 jet fuel using methods known to those skilled in the art of biomass refining [U.S. DOE Energy Efficiency & Renewable Energy Biomass Program, "National Algal Biofuels Technology Roadmap", May 2010]. Cell-free broth, which has passed through the cell mass removing filters, can then be subjected to any necessary additional waste removal treatments, which depends on the source of flue gas. The remaining water and nutrients can then be pumped back into the digesters.

Rhodococcus opacus strains have extremely versatile metabolisms, making them capable of heterotrophic, as well as chemoautotrophic growth. In certain embodiments of the present invention the heterotrophic capability of Rhodococcus opacus is exploited to further improve the efficiency of energy and carbon conversion to lipid product. The non-lipid biomass remainder following lipid extraction is composed of primarily protein and carbohydrate. In certain embodiments of the present invention, some of the carbohydrate and/or protein remainder following lipid extraction is acid hydrolyzed to simple sugars and/or amino acids, the acid is neutralized, and the solution of simple sugars and/or amino acids are fed to a second heterotrophic bioreactor containing Rhodococcus opacus that consumes the biomass input and produces additional lipid product, as illustrated in FIG. 10.

Figure 2:
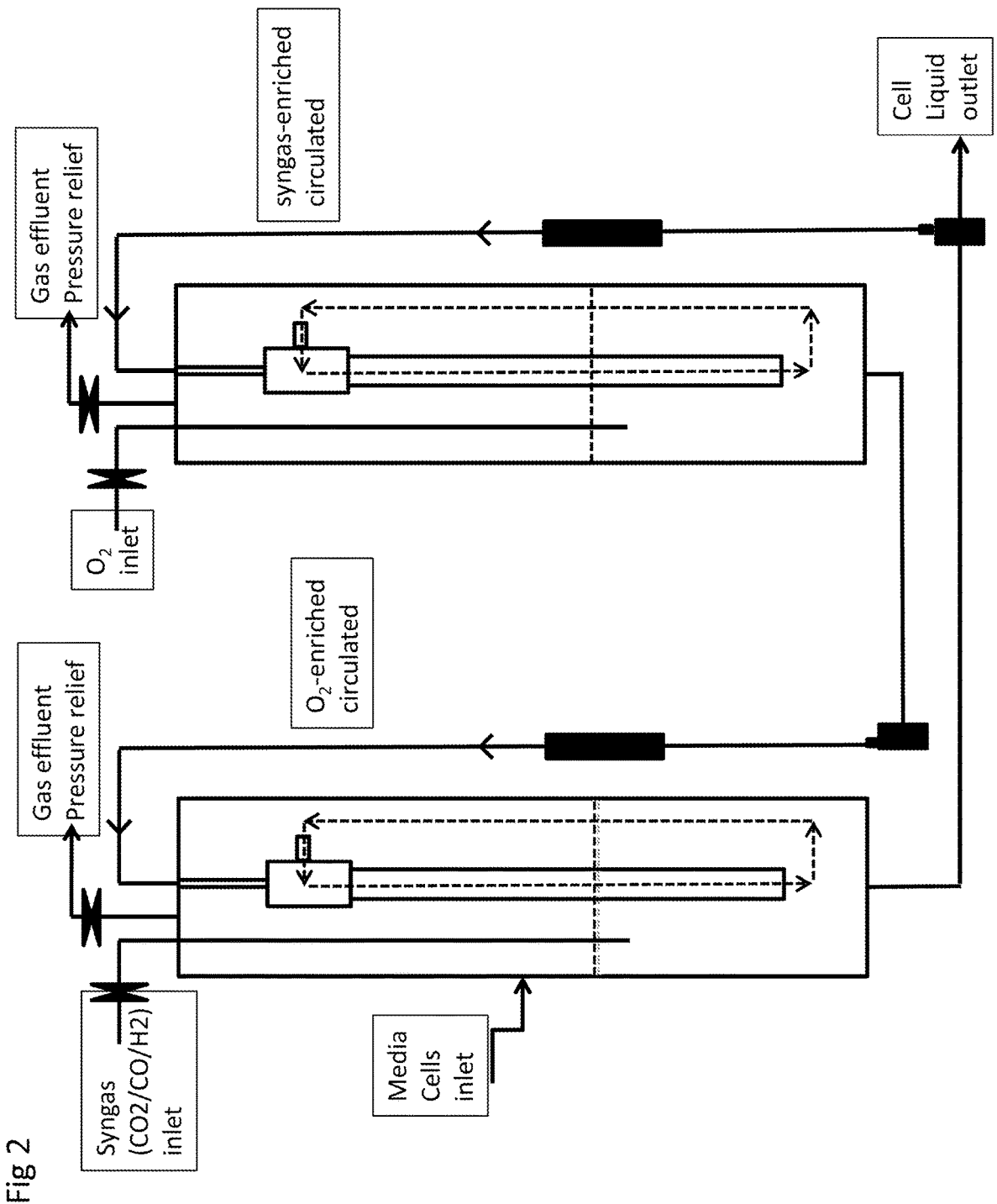
FIG. 2 is a diagram of two reactors of the present invention connected in series, where outflow of reactor 1 is fed into reactor 2. In certain embodiments each reactor may have different compositions of gas delivered to it.
Figure 3:
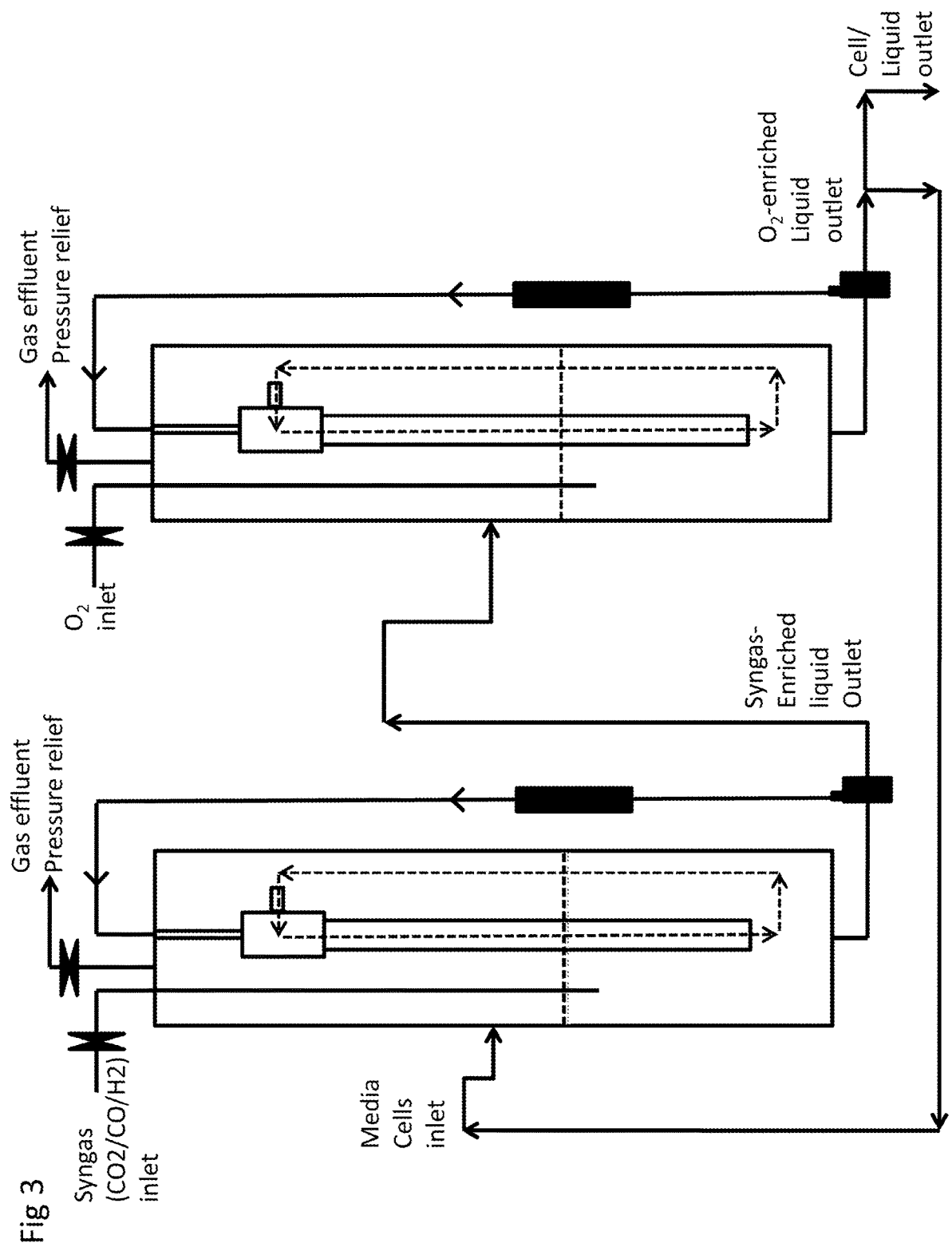
FIG. 3 is a diagram of two reactors connected in series, where outflow of reactor 1 is recirculated or fed into reactor 2. Outflow from reactor 2 is recirculated or cycled back to reactor 1. In certain embodiments each reactor may have different compositions of gas delivered to it.

FIGS. 2 and 3 include an exemplary schematic diagram of a bioreactor series, which can be used in certain embodiments. Bioreactor series can be used, for example, as the reactor illustrated as Box 4 in FIG. 8 labeled "Bioreactor—Knallgas Microbes" and/or as the reactor illustrated as Box 4 in FIG. 9 labeled "Bioreactor—Oleaginous knallgas bacteria." The bioreactor series illustrated in FIGS. 2 and 3 can be operated to take advantage of the low solubilities of hydrogen, carbon monoxide and oxygen gas in water and avoids dangerous mixtures of hydrogen or carbon monoxide and oxygen gas. In addition, the bioreactor can provide the oxyhydrogen microorganisms used in this particular embodiment with the oxygen and hydrogen needed for cellular energy and carbon fixation, for example, by sparging and bubbling the gases into the vertical liquid columns filled with culture medium.

The bioreactor series in FIGS. 2 and 3 include a first bioreactor and a second bioreactor. In the set of embodiments illustrated in FIGS. 2 and 3, syngas (CO2/CO/H2) is introduced to the first bioreactor (left reactor) while oxygen is introduced to second column (right reactor), although in other embodiments, their order may be reversed. The oxygen and/or hydrogen and/or syngas are introduced to their respective columns of liquid by sparging and bubbling, such that they travel upwards through the culture medium. The bioreactor series can include horizontal liquid connection from the bottom of each respective column connecting to the other column.

Headspaces of the first and second reactors can be isolated from each other by the liquid medium. In some embodiments, the low solubility of the gases in the liquid medium allow for the collection of gases at the tops of the columns after bubbling or diffusing the gases up through their respective columns Establishing isolated headspaces can prevent a dangerous amount of hydrogen or carbon monoxide and oxygen gases from mixing with each other. For example, the hydrogen or carbon monoxide gas in one bioreactor can be prevented from mixing with the oxygen gas in the other bioreactor (and vice versa) Inhibiting mixing of the hydrogen and oxygen gases can be achieved, for example, by maintaining the connections between the two bioreactors such that they are filled with liquid, thereby preventing transport of the gases from one bioreactor to the other.

In some such embodiments, any unused hydrogen gas and/or syngas that passes through the culture medium without being taken up by the microorganisms (and which may end up in the head space) can be recirculated by pumping the gas out of the headspace, and pumping it back into the medium at the bottom of the liquid column through the eductor or venturi. In some embodiments, the oxygen and/or air might similarly be recirculated on its respective side or alternatively vented after passing through the headspace.

The oxyhydrogen microorganisms are allowed to freely circulate along with the liquid medium between the first and second bioreactors in certain embodiments. In other embodiments, the oxyhydrogen microorganisms are restricted to the hydrogen and/or syngas side, for example, by using a microfilter that retains the microorganisms on the hydrogen side but allows the liquid medium to pass through.

The bioreactor arrangement in series can take advantage of the relatively high solubility of carbon dioxide in certain embodiments and/or the strong ability of oxyhydrogen microorganism to capture carbon dioxide from relatively dilute streams in certain embodiments. The operation in such embodiments can exploit the carbon concentrating mechanism native to oxyhydrogen microbes. Flue gas and/or air containing carbon dioxide can be transported through the oxygen side of the bioreactor series. The carbon dioxide can be dissolved into solution and/or taken up by the oxyhydrogen microbes and subsequently transported over to the hydrogen side of the bioreactor, for example, through the horizontal liquid connection. On the hydrogen side, reducing equivalents can be provided that drive fixation of the carbon. In some embodiments, other gases pumped in on the oxygen side (e.g., oxygen, nitrogen, etc.) have a low solubility relative to $CO_2$, and are carried over to the hydrogen side to a much lesser extent. Rather than being passed from the right column to the left column, the low solubility gases can be transported to headspace of the right column. In some embodiments, after the low solubility gases (e.g. oxygen and nitrogen) are transported to headspace, they can be vented.

The following documents are incorporated herein by reference in their entirety for all purposes: U.S. Provisional Patent Application No. 61/570,773, filed Dec. 14, 2011 and entitled "METHOD AND APPARATUS FOR GROWING MICROBIAL CULTURES THAT REQUIRE GASEOUS ELECTRON DONORS, ELECTRON ACCEPTORS, CARBON SOURCES, OR OTHER NUTRIENTS"; International Patent Application No. PCT/US2011/34218, filed Apr. 27, 2011, and entitled "USE OF OXYHYDROGEN MICROORGANISMS FOR NON-PHOTOSYNTHETIC CARBON CAPTURE AND CONVERSION OF INORGANIC AND/OR C1 CARBON SOURCES INTO USEFUL ORGANIC COMPOUNDS"; International Patent Application Serial No. PCT/US2010/001402, filed May 12, 2010, entitled "BIOLOGICAL AND CHEMICAL PROCESS UTILIZING CHEMOAUTOTROPHIC MICROORGNISMS FOR THE CHEMOSYTHETIC FIXATION OF CARBON DIOXIDE AND/OR OTHER INORGANIC CARBON SOURCES INTO ORGANIC COMPOUNDS, AND THE GENERATION OF ADDITIONAL USEFUL PRODUCTS"; and U.S. Patent Application Publication No. 2010/0120104, filed Nov. 6, 2009, entitled "BIOLOGICAL AND CHEMICAL PROCESS UTILIZING CHEMOAUTOTROPHIC MICROORGNISMS FOR THE CHEMOSYTHETIC FIXATION OF CARBON DIOXIDE AND/OR OTHER INORGANIC CARBON SOURCES INTO ORGANIC COMPOUNDS, AND THE GENERATION OF ADDITIONAL USEFUL PRODUCTS.

The following examples are intended to illustrate certain embodiments of the present invention, but do not exemplify the full scope of the invention.

Example

Prototype Gas-Mixing Bioreactor
Description of Principles of Pressurized Operation and Gas Mixing This reactor design addresses limitations in mass transfer of gases from the reactor headspace into the liquid phase, where the microbes reside. This is particularly relevant when attempting to address gas demand for extremely dense cultures when demand for the gas or gases is higher than is able to diffuse into the liquid phase. In some embodiments the energy substrates and/or the carbon source and/or electron acceptors are provided in gaseous form.

In a conventional bioreactor/fermenter design the electron accepting gas (usually O2 in air) is sparged through the media in a one-pass system. This allows the concentration of O2 to remain as high as possible and is an effective means to deliver O2 at low cell densities.

Air recirculation systems can be used to increase the number of passes (volumes of gas per volumes of media per time) in the typical bioreactor design, but greater gas mixing will not necessarily lead to better growth conditions as the O2 partial pressure in the gas phase will also decrease, thus slowing the rate of transfer. In sum the recirculation of air in a conventional fermenter will be an inefficient use of power as the energy would be better spent pumping in fresh air with ~21% O2 as opposed to using the same amount of energy to recirculate O2 at lower saturation values.

Conventional type bioreactors also rely on impeller mixing systems and various types of baffles to more efficiently drive O2 gas into the media but are limited in their effectiveness and efficient use of power. Impellers are also not well suited to drive headspace gases that have passed through the media back into solution.

Rather than relying on an impeller-type mixer, the bioreactor of the present invention has a liquid circulating pump to power a Venturi unit (for example Venturi model Mazzei 484x, Mazzei Injector Company, LLC, Bakersfield, Calif.) that is used to entrain a headspace gas into the liquid stream and put it into the media, while concomitantly providing solution mixing (See FIG. 1).

In some embodiments the system can be constructed from polymer or stainless steel piping materials and Venturi mixers and circulation pumps. In some embodiments the particular Venturi design may be chosen to entrain differing gas to liquid volume ratios to meet the mixing needs of the particular system.

In some embodiments different gas to liquid mass mixing ratios may be achieved by moderating the total system pressure.

In some embodiments the Venturi unit provides for the formation of extremely fine bubbles that will not form a static foam because, as the foam is created, and moved up through the barrel of the reactor with the bulk air flow to the outlet, it is taken back up by the gas uptake for the Venturi.

In some embodiments using the Venturi mixing unit with commercial piping material (e.g., stainless steel or PVC) allows for the incorporation of cheaper, non-specialty in-line sensors and chemical dosing units. These sensors can easily be used in plumbing bypasses for easier maintenance and repair, alleviating the need to shut down the reactor during runs. Commercial piping ensures the safe operation of industrial, municipal and domestic water and gas pipes. Thus, the reactor in the present invention may be operated at greater pressures than conventional fermentation units due to the robust material used in the design of commercial piping.

The type of solution mixing used in the present invention allows bioreactors geometries in certain embodiments with higher aspect ratio then conventional type bioreactors, which facilitates operation at elevated pressures due to the reduced cylindrical radius of the reactor volume, and which reduces footprint size in certain embodiments.

Bioreactor operating pressure and gas transfer rate.

In some embodiments improved gas transfer is attained by running the reactor above ambient pressure. The rate of transfer of a gas phase component into the aqueous phase is determined by Equation 1.

$$\text{Gas transfer rate} = KLa(C^*L - CL) \quad (1)$$

Figure 7:
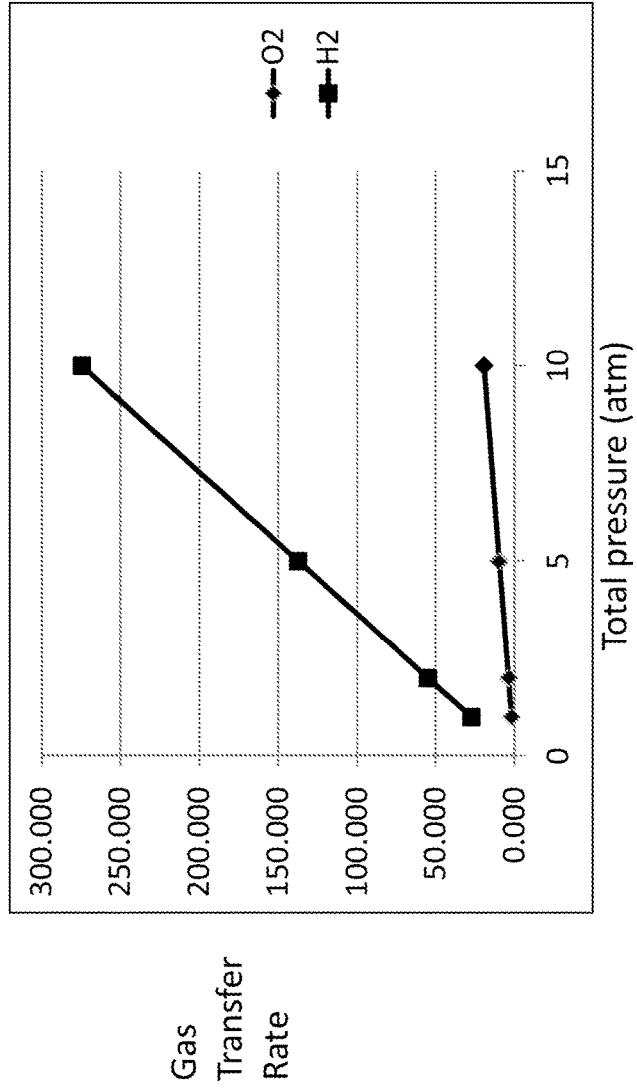
FIG. 7 is a graph showing how pressure can be used in certain embodiments of the present invention to improve gas transfer into media, as governed by reactor headspace pressure. The gas transfer rate increases with increased reactor pressure as evidenced in the gas transfer rate equations. The mass transfer of hydrogen and oxygen given a gas mix of 5% O2 and 65% H2, and the remainder being 20% N2 and 10% CO2, is given as a non-limiting embodiment of the type of gas that may be used in the present invention.

KLa=liquid mass-transfer coefficient times the available surface area $C^*L$=dissolved gas concentration in equilibrium with pressure in gas phase CL=dissolved gas concentration in the aqueous phase The KLa factor is inherent to the system design parameters and can be modified by incorporating types of mixing and flow rates. The rate of transfer of a gas to the aqueous phase (constant KLa) can be affected by the fact that the gas phase concentration is proportional to the partial pressure of the individual gas components. For example, FIG. 7 shows the effect on mass transfer by elevating pressure for a gas mix of 5% O2 and 65% H2, and the remainder being 20% N2 and 10% CO2. At ambient sea-level pressure (1 atmosphere), ($C^*L-CL$) for O2 and H2 are 1.9 and 27.5, respectively, at equilibrium.

Example

Cultivation Using Prototype Reactor System with Gaseous Electron Acceptor

Experimental Purpose:

1) Test the principle of the reactor design: effect of centrifugal pump and Venturi apparatus on growing bacterial cells.
2) Test pH control system to determine integrity of reactor operating at moderately elevated pressures (15 psi).

Experimental Run:

Cell type/strain: A knallgas microorganism within one of the genera listed in claim 2 with inoculum, *Rhodococcus opacus* (DSM 43205) with inoculum initially grown on sugar Energy source: glucose carbohydrate substrate 40 g/L in minimal salts medium (MSM)

Air supply: O2 supplied depending on O2 demand, pressure controlled but air flow rate not measured.

Media: 1 L

Carbon source: glucose pH adjusted by addition of 8N NH4OH by automated dosing to maintain pH=6.8.

Glucose was supplied at substrate 40 g/L in minimal salts medium (MSM) and air supplied through modified inlet in the liquid circulation loop at P=10-25 psi depending on O2 demand.

Protocol:

1) 1 L media put into reactor
2) inoculated with 50 ml glucose-grown *R. opacus* cells
3) t=0; OD=0.25; T=30 C+/-2 C
4) pH maintained at 6.8 by automated addition of 8N NH4OH
5) Time course of 96 hours
6) Continuous monitoring of optical density (OD), pH, and dissolved oxygen (DO).
7) t=96 hours; OD=6.25. (cell density=9 g dry weight/L)

Example

Cultivation with Gas Carbon Source and Electron Donor (H2/CO2) Feedstock

Experimental Purpose: test prototype reactor with H2/CO2

Experimental Run:

Cell type/strain: Knallgas microorganism within one of the genera listed in claim 2, *Rhodococcus opacus* (DSM 43205) with inoculum initially grown on gas Energy source: Gas mix: H2 (80%)/CO2 (10%)/air (10%) for a total O2 concentration of 2.0%, in minimal salts medium (MSM)

Air supply: O2 supplied depending on O2 demand, maintained at 5.25% via DO measurement, pressure controlled but air flow rate not measured.

Media: 1 L

Carbon source: CO2 gas pH adjusted by addition of 8N NH4OH by automated dosing to maintain pH=6.8.

Gas mix in minimal salts medium (MSM) and air supplied through modified inlet in the liquid circulation loop; flow rate to maintain optimal O2 concentration supplied by the mass flow controller.

Protocol:
1) 1 L media put into reactor
2) inoculated with 50 ml H2-grown knallgas microbial *R. opacus* cells
3) t=0; OD<0.1; T=30 C+/−0.5 C
4) pH maintained at 6.8 by automated addition of 8N NH4OH
5) Time course of 96 hours
6) Continuous monitoring of optical density (OD), pH, and dissolved oxygen (DO).

Example

Growth of Representative Oxyhydrogen Microorganism on H2/CO2 as Sole Carbon and Energy Source.

In this example, an oxyhydrogen microorganism that accumulates the valuable compound polyhydroxybutyrate (PHB) was grown on an inorganic medium with $CO_2$ as the carbon source and hydrogen acting as the electron donor while oxygen provides the electron acceptor. Oxyhydrogen microbes such as these can be used in certain embodiments of the present invention in converting C1 chemicals such as carbon dioxide into longer chain organic chemicals.

Static anaerobic reaction vessels were inoculated with *Cupriavidus necator* DSM 531 (which can accumulate a high percentage of cell mass as PHB). The inoculum were taken from DSM medium no. 1 agar plates kept under aerobic conditions at 28 degrees Celsius. Each anaerobic reaction vessel had 10 ml of liquid medium DSM no. 81 with 80% $H_2$, 10% $CO_2$ and 10% $O_2$ in the headspace. The cultures were incubated at 28 degrees Celsius. The *Cupriavidus necator* reached an optical density (OD) at 600 nm of 0.98 and a cell density of $4.7 \times 10^8$ cells/ml after 8 days.

Another growth experiment was performed for *Cupriavidus necator* (DSM 531). The medium used for growth was the mineral salts medium (MSM) formulated by Schlegel et al. The MSM medium was formed by mixing 1000 ml of Medium A, 10 ml of Medium B, and 10 ml of Medium C. Medium A included 9 g/l $Na_2HPO_4.12H_2O$, 1.5 g/l $KH_2PO_4$, 1.0 g/l $NH_4Cl$, 0.2 g/l $MgSO_4.7H_2O$, and 1.0 ml of Trace Mineral Medium. The Trace Mineral Medium included 1000 ml distilled water; 100 mg/l $ZnSO_4.7H_2O$; 30 mg/l $MnCl_2.4H_2O$; 300 mg/l $H_3BO_3$; 200 mg/l $COCl_2.6H_2O$; 10 mg/l $CuCl_2.2H_2O$; 20 mg/l $NiCl_2.6H_2O$; and 30 mg/l $Na_2MoO_4.2H_2O$. Medium B contained 100 ml of distilled water; 50 mg ferric ammonium citrate; and 100 mg $CaCl_2$. Medium C contained 100 ml of distilled water and 5 g $NaHCO_3$. The cultures were grown in 20 ml of MSM media in 150-ml stopped and sealed serum vials with the following gas mixture in the headspace: 71% Hydrogen; 4% Oxygen; 16% Nitrogen; 9% Carbon dioxide. The headspace pressure was 7 psi. The cultures were grown for eight days at 30 degrees Celsius. *Cupriavidus necator* reached an OD at 600 nm of 0.86.

Example

Inoculation and Growth Conditions

Organisms from the genus *Rhodococcus* and from the genus *Cupriavidus* were tested for their ability to grow on different carbon sources including gaseous carbon sources. Colonies from strains grown on LB agar plates at 30° C. were transferred into flasks containing 10% (v/v) of the indicated media for 3-20 days at 30° C. and 250 rpm. *R. opacus* strain DSM 44193 exhibited growth only under heterotrophic growth conditions as measured by optical density (OD) at 650 nm on MSM medium (1 L Medium A:9 g Na2HPO412H2O, 1.5 g H2PO4, 1.0 g NH4Cl and 0.2 g MgSO4.7H2O per 1 L; 10 ml Medium B:50 mg Ferric ammonium citrate and 100 mg CaCl2 per 100 ml; 10 ml Medium C:5 g NaHCO3 per 100 ml; and 1 ml Trace Mineral Solution:100 mg ZnSO4.7H2O, 30 mg MnCl2. 4H20, 300 mg H3BO3, 200 mg COCL2.6H20, 10 mg CuCl2.2H2O, 20 mg NiCl2.6H2O and 30 mg Na2MoO4.2H2O per 1 L) supplemented with 40 g/L glucose. *R. opacus* strain DSM 43205 showed identical growth rates under heterotrophic conditions reaching O.D=9.0. Strain DSM 43205 was also able to grow on chemoautotrophic conditions (MSM medium supplemented with 66.7% H2, 9.5% CO2, 5% O2 and 18.8% N2) and heterotrophically on a single carbon compound as the solely carbon source (MSM medium supplemented with 25 g/l methanol). *Rhodococcus* sp. (DSM 3346) exhibited growth under heterotrophic conditions and chemoautotrophic conditions (DSMZ Medium 81: 1 L of Mineral Medium for chemolithotrophic growth: 2.9 g Na2HPO4.2H2O, 2.3 g KH2PO4, 1.0 g NH4Cl, 0.5 g MgSO4.7H2O, 0.5 g NaHCO3, 0.01 g CaCl.2H2O and 0.05 g Fe(NH4) citrate per 1 L; and 5 ml Trace Mineral Solution, supplemented with 80% H2, 10% CO2 and 10% O2). *Cupriavidus necator* (DSM 531) was able to grow under heterotrophic and chemoautotrophic conditions (media described for Strain DSM 43205).

Example

Lipid Profiles

Production of Fatty Acid

Under heterotrophic growth conditions strains *Rhodococcus* strains DSM 44193, DSM 43205, DSM 3346 and DSM 531 produce lipid. Lipid content determined by gas chromatography analysis of cells harvested after 72 hr (unless otherwise indicated) showed over 19% of cellular dry matter (CDM) determined gravimetrically for strains DSM 44193, DSM 43205 and DSM 3346. The lipid content of DSM 43205 was higher than 10% of under chemoautotrophic conditions. Under heterotrophic growth conditions the fatty acid carbon chain length distribution of DSM 44193 is 32%, 26% and 21% of 16, 17 and 18-carbon fatty acid respectively. DSM43205 produces similar proportions of 16, 17 and 18-carbon fatty acid (30%, 24% and 32% respectively).

Chemoautotrophic growth condition significantly reduces the 17-carbon fatty acid abundance (6%) and maintains similar levels of 16 and 18-carbon fatty acid (36% and 27% respectively). DSM3346 exhibits similar fatty acid distribution of 16, 17 and 18-carbon fatty acid (39%, 24% and 25% respectively) under heterotrophic growth. Chemoautotrophic growth condition significantly increases the 16-carbon fatty acid levels (66%) and reduces the 17 and 18-carbon fatty acid levels (4%, 14%).

Example

Analysis of fatty acids from the cell pellet is carried out in 25 mm×150 mm glass tube in the presence of 50 μL of Eicosane standard (approx 200 μg/mL) and 50 μL lipid standard (~200 ug/ml). Pellet is extracted with 5 ml chloroform, 10 ml methanol, 4 ml phosphate buffer (phosphate buffer reagent: 50 mM, pH 7.4, 8.7 g K2HPO4 in 1 L water, and about 2.5 mL 6N HCl to adjust pH=7.4, and 50 ml chloroform per 1 L buffer). The mixture is vortexed for 30 sec, sonicated for 2 min and incubated in dark for at least 3 hr. Phases are separated in the presence of 5 ml chloroform and 5 ml ddH2O, vortexed and spun down 2000 rpm for 1 min. The bottom layer is transferred with a glass Pasteur pipette to clean 16 mm×125 mm glass tube with Teflon-lined screw top and dried under N2. The dried extract is re-suspended 1.5 ml of a 10:1:1 mixture of Methanol:CHCl3:concentrated HCl, vortexed and incubated in 60° C. for 14-16 hr (overnight). The extracts are cooled and 2 ml of ddH2O and 2 ml of hexane are added, vortexed and centrifuged for 5 min at 2000 rpm for phase separation. The top hexane layer is transferred to clean 16 mm tube. An additional two hexane extractions (vortex, centrifugation and phase separation) will be carried out in the extract tube. The hexane extracts are dried in a GC vial and analyzed by Gas Chromatography for the presence of fatty acids, including but not limited to dodecanoic acid.

Example

Experimental Purpose:
  Test the principle of the reactor design: effect of centrifugal pump and Venturi apparatus on growing bacterial cells.
  Test cultivation using pure glycerol as a carbon source vs. crude glycerol from biodiesel manufacturing
Experimental Run:
  Cell type/strain: A knallgas microorganism within the Rhodococcus genera (*Rhodococcus opacus*), which is able to accumulate lipids>20% by weight with glycerol-grown inoculum (50 ml)
  1 L venturi reactor, 500 ml working volume
  Energy and carbon source: Reactor 1 started with 20 g/L glycerol. Reactor 2 started with 20 g/L crude glycerol. Glycerol added with syringe pump to maintain >10 g/L
  Media: 500 ml minimal salts medium (MSM)
  Air supply: O2 supplied depending on O2 demand, pressure controlled but air flow rate not measured.
  pH adjusted by addition of 2N NH4OH
  Minerals added as a function of N usage
Protocol:
  500 ml media put into reactor
  inoculated with 50 ml glucose-grown TKO2 cells
  t=0; OD=0.25; T=30 C+/−2 C
  pH maintained at 7.0 by manual addition of 2N NH4OH
  Time course of 180 hours
  Continuous monitoring of optical density (OD), pH, and dissolved oxygen (DO).
System/Experiment Observations:
  Maximum cell density: Reactor 1=10.5 g/L, Reactor 2=15.2 g/L
  Analysis of solids in supernatant indicate 2-4 fold more residual soluble organic compounds than in the pellet.

Example

Figure 11:
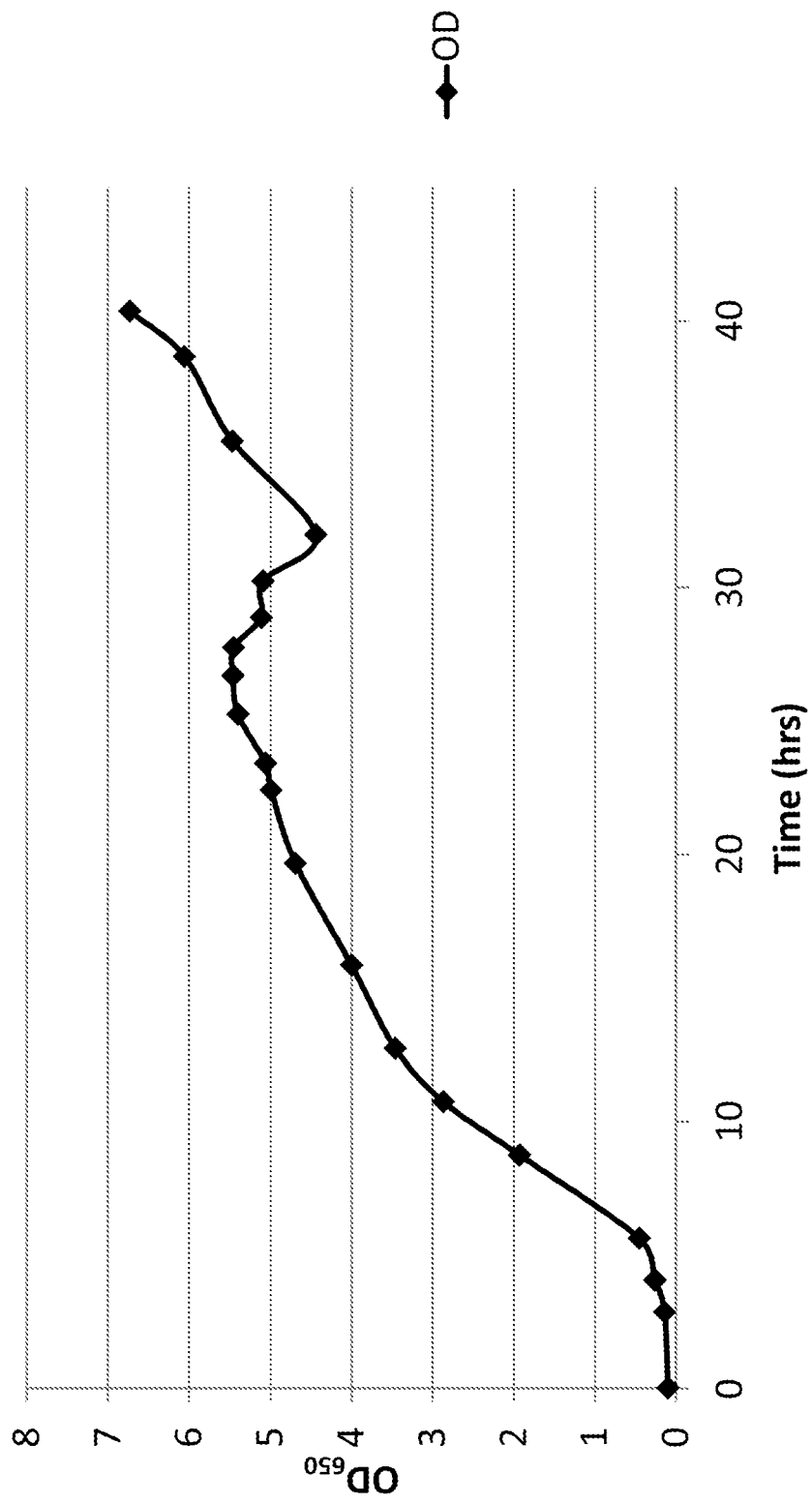
FIG. 11 shows a growth curve as indicated by optical density as a function of time for *Rhodococcus opacus* grown in a prototype 200 liter bioreactor apparatus of one of the embodiments of the present invention.
Figure 12:
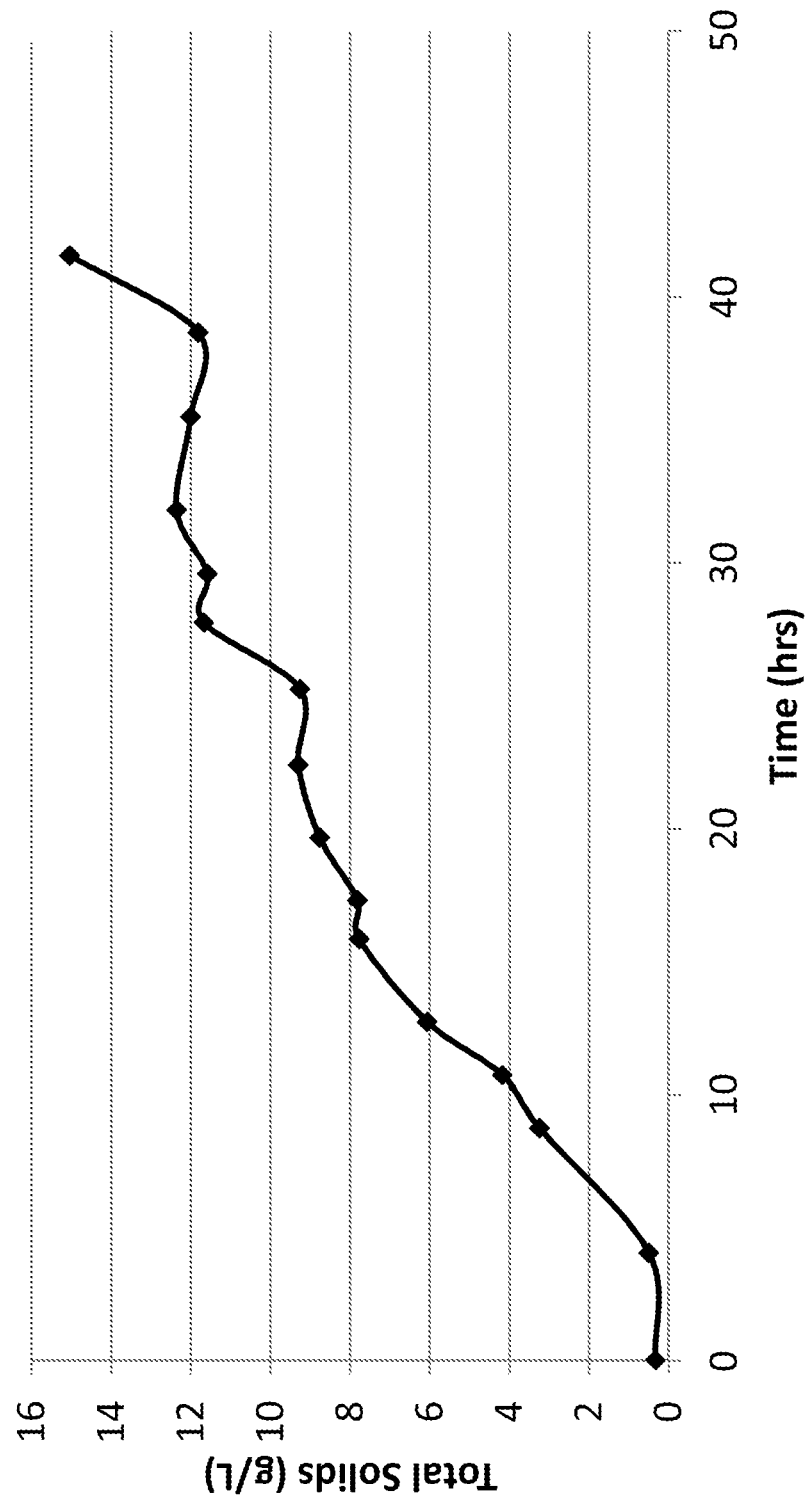
FIG. 12 shows a growth curve as indicated by total solids (grams/liter) as a function of time for *Rhodococcus opacus* grown in a prototype 200 liter bioreactor apparatus of one of the embodiments of the present invention.

Experimental Purpose:
  Test the principle of the reactor design: effect of centrifugal pump and Venturi apparatus on growing bacterial cells.
  Runs to test pure glycerol vs. crude glycerol, which is a byproduct of biodiesel manufacturing (includes glycerol, methanol, salts, and Matter Organic Non Glycerine (MONG))
Experimental Run:
  Cell type/strain: A knallgas microorganism within the Rhodococcus genera (*Rhodococcus opacus*) with glycerol-grown inoculum (50 ml)
  1 L Venturi bioreactor design, 500 ml working volume
  Energy and carbon source: Reactor 1 started with 40 g/L glycerol. Reactor 2 started with 20 g/L crude glycerol.
  Media: 500 ml minimal salts medium (MSM)
  Air supply: O2 supplied depending on O2 demand, pressure controlled but air flow rate not measured.
  50 ml inoculated TKO2 grown on glycerol.
  Minerals added as a function of N usage
  Both reactors received a total of 6 g/L NH4Cl initially and in total.
Protocol:
  500 ml media put into reactor
  inoculated with 50 ml glucose-grown TKO2 cells
  pH maintained at 7.0 by manual addition of 2N NaHCO3
  Time course of 48 hours
  Continuous monitoring of optical density (OD), pH, and dissolved oxygen (DO).
System/Experiment Observations:
  After 80 hours Nitrogen was not detectable.
  Maximum cell density: Reactor 1=9 g/L, Reactor 2=15 g/L Example Experimental Purpose:
  Test the principle of the reactor design: effect of centrifugal pump and Venturi apparatus on growing bacterial cells.
  Test ability to scale the venturi reactor to 200 L (100 L working volume)
Experimental Run:
  Cell type/strain: A knallgas microorganism within the Rhodococcus genera (*Rhodococcus opacus*) with glycerol-grown inoculum
  Energy and carbon source: 20 g/L initial glycerol. Glycerol added with syringe pump to maintain at least 10 g/L, total glycerol delivered=16.9 kg/100 L.
  Air supply: O2 supplied depending on O2 demand, pressure controlled but air flow rate not measured.
  N maintained at 8 g NH4Cl/L
  pH adjusted by addition of 40 ml of 2N NH4OH then 10N NaOH
  2 L inoculated TKO2 grown on glycerol.
  Minerals added as a function of N usage Protocol:
 100 L media put into reactor
 inoculated with 2 L glucose-grown TKO2 cells
 t=0; OD=0.25; T=30 C+/−2 C
 pH maintained manually at 7.0+/−0.1
 Time course of 120 hours
 Continuous monitoring of optical density (OD), pH, and dissolved oxygen (DO). (see FIG. 11)
System/Experiment Observations:
 Cell density over 10 g/L (see FIG. 12)

Example

Experimental Purpose:
 Test the principle of the reactor design: effect of centrifugal pump and Venturi apparatus on growing bacterial cells.
 Effects of stable glycerol addition during consumption by either varying initial set value or analyzing effect of further addition upon depletion.
Experimental Run:
 Cell type/strain: A knallgas microorganism within the Rhodococcus genera (Rhodococcus opacus) with glycerol-grown inoculum (50 ml)
 Energy and carbon source: 20 g/L initial glycerol. Glycerol added with syringe pump to attempt >10 g/L. Total glycerol delivered=100 g/L Media: 500 ml minimal salts medium (MSM)
 Air supply: O2 supplied depending on O2 demand, pressure controlled but air flow rate not measured.
 pH adjusted w/2N NaHCO3
 50 ml inoculated TKO2 grown on glycerol.
 Minerals added as a function of N usage
 4 g/L initial NH4Cl
 Three trials tested where NH4Cl adjusted to a final value of 4 (Trial 1), 6 (Trial 2), and 8 (Trial 3)
Protocol:
 500 mL media put into reactor
 inoculated with 50 ml glucose-grown TKO2 cells
 t=0; OD=0; T=30 C+/−2 C
 pH maintained manually at 7.0+/−0.1
 Time course of 90 hours
 Continuous monitoring of optical density (OD), pH, and dissolved oxygen (DO).
System/Experiment Observations:
 Cell density achieved for different NH4Cl adjustment trials: Trial 1=8.85 g/L,
 Trial 2=21.6 g/L, and Trial 3=16 g/L
 Volatile solids/total solids values over 94% achieved Example Experimental Purpose:
 Test the principle of the reactor design: effect of centrifugal pump and Venturi apparatus on growing bacterial cells.
 Test effects of varying Nitrogen
 Effects of stable glycerol addition as consumed with set initial nitrogen or further addition upon depletion.
Experimental Run:
 Cell type/strain: A knallgas microorganism within the Rhodococcus genera
 (Rhodococcus opacus) with glycerol-grown inoculum (50 ml)
 Energy and carbon source: 20 g/L initial glycerol.
 Glycerol added with syringe pump to maintain >10 g/L.
 Media: 500 ml minimal salts medium (MSM)
 Air supply: O2 supplied depending on O2 demand, pressure controlled but air flow rate not measured.
 pH adjusted by addition of 2N NaOH to (reactors 1&2) by automated dosing to maintain pH=7+/−0.1, 2N NaCO3 to (reactors 3&4)
 50 ml inoculated TKO2 grown on glycerol.
 Minerals added as a function of N usage
Protocol:
 500 mL media put into reactor
 inoculated with 50 ml glycerol-grown TKO2 cells
 pH maintained at 7.0 by automated addition of 2N NaOH or NaCO3
 Time course of 48 hours
 4 Trials tested with varying NH4Cl levels: g NH4Cl/L at 4 (Trial 1), 4-6 (Trial 2), 4-8 (Trial 3), 4-12 (Trial 4)
 Continuous monitoring of optical density (OD), pH, and dissolved oxygen (DO).
System/Experiment Observations:
 Growth proceeded without a lag
 Cell density results—Trial 1=8.5 g/L; Trial 2=11.5 g/L, Trial 3=8.74 g/L; and Trial 4=15.3 g/L Specific preferred embodiments of the present invention have been described here in sufficient detail to enable those skilled in the art to practice the full scope of invention. However it is to be understood that many possible variations of the present invention, which have not been specifically described, still fall within the scope of the present invention and the appended claims. Hence these descriptions given herein are added only by way of example and are not intended to limit, in any way, the scope of this invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer to, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively.

What is claimed is:

1. An apparatus comprising two or more reactor vessels in fluid communication with each other, comprising:
    a first reactor vessel and a second reactor vessel each comprising: (i) a reaction chamber having an upper portion comprising a gas head space, and a lower portion comprising a biological growth chamber adapted to receive one or more reaction components comprising a liquid phase, a microorganism, and/or an extract of a microorganism; and (ii) a gas inlet that is positioned to introduce gas into the biological growth chamber;
    a first recirculation conduit that extends from the lower portion of the first reactor vessel to the upper portion of the second reaction vessel, and which is adapted to allow one or more reaction components from the biological growth chamber of the first reactor vessel to circulate from the lower portion of the first reactor vessel to the lower portion of the second reactor vessel via a route that exposes the one or more reaction components to gas contained in the gas head space of the second reactor vessel,
    wherein the first recirculation conduit extends from the lower portion of the first reactor vessel through the upper portion of the second reactor vessel and terminates in the lower portion of the second reactor vessel,
    wherein the portion of the first recirculation conduit that extends through the upper portion of the second reaction vessel includes a first gas recirculation inlet adapted to draw gas from the gas head space of the second reactor vessel into the first recirculation conduit; and
    a second recirculation conduit that extends from the lower portion of the second reactor vessel to the upper portion of the first reaction vessel, and which is adapted to allow one or more reaction components from the biological growth chamber of the second reactor vessel to circulate from the lower portion of the second reactor vessel to the lower portion of the first reaction vessel via a route that exposes the one or more reaction components to gas contained in the gas head space of the first reactor vessel,
    wherein the second recirculation conduit extends from the lower portion of the second reactor vessel through the upper portion of the first reaction vessel and terminates in the lower portion of the first reactor vessel,
    wherein the portion of the second recirculation conduit that extends through the upper portion of the first reactor vessel includes a second gas recirculation inlet adapted to draw gas from the gas headspace of the first reactor vessel into the second recirculation conduit,
    wherein a first gas composition is introduced into the gas inlet of the first reactor vessel and a second gas composition is introduced into the gas inlet of the second reactor vessel, and wherein a combination of the first gas composition and the second gas composition would comprise an explosive gas composition if mixed together,
    wherein the first and second reactor vessels comprise first and second gas headspaces, respectively, which are isolated from one another such that they are not in direct fluid communication, and are adapted to maintain the first and second gas compositions spatially separated in the first and second reactor vessels,
    wherein at least one of the first and second gas compositions comprises an inorganic or organic carbon source, and
    wherein the first and second recirculation conduits are adapted to facilitate the circulation of the one or more reaction components between the first and second reactor vessels to alternately expose the one or more reaction components to the first and second gas compositions.

2. An apparatus according to claim 1, wherein a microorganism and/or an extract of a microorganism circulates along with a liquid phase between the first and second reactor vessels, wherein the concentrations of dissolved gases from the first and second gas compositions to which the microorganism and/or extract is exposed varies over time.

3. An apparatus according to claim 1, wherein said inorganic or organic carbon source is utilized by a microorganism and/or an extract of a microorganism as a carbon source for growth, biosynthesis, fermentation, and/or conversion into at least one organic compound.

4. An apparatus according to claim 3, wherein biological utilization and/or conversion of the carbon source by the microorganism and/or extract comprises: uptake of the carbon source from the gaseous phase; providing a gaseous electron donor for the purpose of generating intracellular reducing equivalents or intracellular energy; providing a gaseous electron acceptor for the purpose of generating intracellular energy; and/or providing a nutrient that exists in the gaseous phase under room temperature and atmospheric pressure.

5. An apparatus according to claim 1, wherein at least one of the first and second gas compositions is generated chemically, thermochemically, and/or electrochemically, and/or is taken or derived from an industrial, agricultural, forestry, mining, oil and gas drilling, or municipal waste stream or pollutant, and/or is a gas that naturally occurs or occurs as a pollutant in the earth's atmosphere.

6. An apparatus according to claim 3, wherein the microorganism comprises a knallgas and/or chemoautotrophic and/or methanotrophic microorganism.

7. An apparatus according to claim 6, wherein the microorganism comprises a knallgas microorganism selected from: *Rhodopseudomonas* sp.; *Rhodospirillum* sp.; *Rhodococcus* sp.; *Rhizobium* sp.; *Thiocapsa* sp.; *Pseudomonas* sp.; *Nocardia* sp.; *Hydrogenomonas* sp.; *Hydrogenobacter* sp.; *Hydrogenovibrio* sp.; *Helicobacter* sp.; *Xanthobacter* sp.; *Hydrogenophaga* sp.; *Bradyrhizobium* sp.; *Ralstonia* sp.; *Gordonia* sp.; *Mycobacteria* sp.; *Alcaligenes* sp.; *Cupriavidus* sp.; *Variovorax* sp.; *Acidovorax* sp.; *Anabaena* sp.; *Scenedesmus* sp.; *Chlamydomonas* sp., *Ankistrodesmus* sp., *Rhaphidium* sp., and combinations thereof;

wherein the microorganism comprises a chemoautotrophic microorganism selected from: *Acetoanaerobium* sp.; *Acetobacterium* sp.; *Acetogenium* sp.; *Achromobacater* sp.; *Acidianus* sp.; *Acinetobacer* sp.; *Actinomadura* sp.; *Aeromonas* sp.; *Alcaligenes* sp.; *Alcaligenes* sp.; *Arcobacter* sp.; *Aureobacterium* sp.; *Bacillus* sp.; *Beggiatoa* sp.; *Butyribacterium* sp.; *Carboxydothermus* sp.; *Clostridium* sp.; *Comamonas* sp.; *Dehalobacter* sp.; *Dehalococcoide* sp.; *Dehalospirillum* sp.; *Desulfobacterium* sp.; *Desulfomonile* sp.; *Desulfotomaculum* sp.; *Desulfovibrio* sp.; *Desulfursarcina* sp.; *Ectothiorhodospira* sp.; *Enterobacter* sp.; *Eubacterium* sp.; *Ferroplasma* sp.; *Halothibacillus* sp.; *Hydrogenobacter* sp.; *Hydrogenomonas* sp.; *Leptospirillum* sp.; *Metallosphaera* sp.; *Methanobacterium* sp.; *Methanobrevibacter* sp.; *Methanococcus* sp.; *Methanosarcina* sp.; *Micrococcus* sp.; *Nitrobacter* sp.; *Nitrosococcus* sp.; *Nitrosolobus* sp.; *Nitrosomonas* sp.; *Nitrosospira* sp.; *Nitrosovibrio* sp. *Nitrospina* sp.; *Oleomonas* sp.; *Paracoccus* sp.; *Peptostreptococcus* sp.; *Planctomycetes* sp.; *Pseudomonas* sp.; *Ralsontia* sp.; *Rhodobacter* sp.; *Rhodococcus* sp.; *Rhodocyclus* sp.; *Rhodomicrobium* sp.; *Rhodopseudomonas* sp.; *Rhodospirillum* sp.; *Shewanella* sp.; *Streptomyces* sp.; *Sulfobacillus* sp.; *Sulfolobus* sp.; *Thiobacillus* sp.; *Thiomicrospira* sp.; *Thioploca* sp.; *Thiosphaera* sp.; *Thiothrix* sp.; and combinations thereof; and/or wherein the microorganism comprises a methanotrophic microorganism.

8. An apparatus according to claim 1, wherein the first and second reactor vessels comprise first and second liquid phases in the lower portions of the first and second reactor vessels, respectively, and wherein the apparatus comprises a horizontal liquid connection between the bottoms of the first and second liquid phases that provides a fluid connection between the first and second liquid phases.

9. An apparatus according to claim 1, wherein a microorganism and/or an extract of a microorganism is exposed to the first and second gas compositions in temporally separate first and second stages, wherein the gas composition in the first stage is the first gas composition and the gas composition in the second stage is the second gas composition.

10. An apparatus according to claim 1, wherein said inorganic or organic carbon source is $CO_2$.

11. An apparatus according to claim 9, wherein the microorganism or extract is restricted to the first reactor vessel.

12. An apparatus according to claim 1, wherein the first and second gas headspaces are isolated and spatially separated from each other by liquid that fills a fluidic connection between the first and second reactor vessels.

13. An apparatus according to claim 12, wherein the first and second gas compositions are bubbled or diffused up through first and second liquid phases in the first and second reactor vessels, respectively, and wherein low solubility of the gases in the first and second liquid phases results in collection of gases at the tops of the reactor vessels.

14. An apparatus according to claim 12, wherein isolation and spatial separation of the separate gas headspaces by the liquid filling the fluidic connection prevents the mixing of the gas headspaces, thereby preventing the emergence of dangerous or potentially flammable or explosive mixtures of gases in the gas headspaces.

15. An apparatus according to claim 1, wherein the first gas composition is introduced into the first reactor vessel through a first gas feed port into the first gas headspace and the second gas composition is introduced into the second reactor vessel through a second gas feed port into the second gas headspace.

16. The apparatus according to claim 1, wherein the first gas composition comprises $H_2$, CO, syngas, $CH_4$, fuel gas, or a combination thereof, and wherein the second gas composition comprises $O_2$ and/or air.

* * * * *